US012630511B2

(12) United States Patent
Lee et al.

(10) Patent No.: US 12,630,511 B2
(45) Date of Patent: May 19, 2026

(54) BENZAMIDE DERIVATIVE, PREPARATION METHOD THEREFOR, AND PHARMACEUTICAL COMPOSITION COMPRISING SAME AS ACTIVE INGREDIENT FOR PREVENTION OR TREATMENT OF CANCER

(71) Applicant: KOREA RESEARCH INSTITUTE OF CHEMICAL TECHNOLOGY, Daejeon (KR)

(72) Inventors: Kwangho Lee, Daejeon (KR); Jiwon Kim, Daejeon (KR); Byoung Chul Cho, Seoul (KR); Gildon Choi, Daejeon (KR); Jiyeon Yun, Seoul (KR); Chae Won Park, Seoul (KR); Krishna Babu Duggirala, Daejeon (KR); Chong Hak Chae, Daejeon (KR); Seo Young Lee, Daejeon (KR); A Reum Go, Daejeon (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 1099 days.

(21) Appl. No.: 17/637,044

(22) PCT Filed: Nov. 19, 2020

(86) PCT No.: PCT/KR2020/016372

§ 371 (c)(1),
(2) Date: Feb. 21, 2022

(87) PCT Pub. No.: WO2021/101268

PCT Pub. Date: May 27, 2021

(65) Prior Publication Data

US 2022/0281817 A1 Sep. 8, 2022

(30) Foreign Application Priority Data

Nov. 19, 2019 (KR) ........................ 10-2019-0148459

(51) Int. Cl.
*C07D 209/14* (2006.01)
*C07D 209/18* (2006.01)
*C07D 401/12* (2006.01)

(52) U.S. Cl.
CPC ......... *C07D 209/14* (2013.01); *C07D 209/18* (2013.01); *C07D 401/12* (2013.01)

(58) Field of Classification Search
None
See application file for complete search history.

(56) References Cited

U.S. PATENT DOCUMENTS

| | | | | |
|---|---|---|---|---|
| 7,153,867 | B2 * | 12/2006 | Shah | A61P 43/00 514/323 |
| 7,326,791 | B2 * | 2/2008 | Gillard | C07D 417/06 548/309.7 |
| 11,976,059 | B2 * | 5/2024 | Lee | C07D 471/04 |
| 2012/0225880 | A1 | 9/2012 | Jiaang et al. | |
| 2015/0197505 | A1 | 7/2015 | Lelais et al. | |
| 2021/0155604 | A1 | 5/2021 | Li et al. | |

FOREIGN PATENT DOCUMENTS

| | | | | |
|---|---|---|---|---|
| KR | 10-2015-0023555 | A | 3/2015 | |
| WO | WO-2006045756 | A1 * | 5/2006 | A61P 9/08 |
| WO | WO 2009/027392 | A1 | 3/2009 | |
| WO | WO 2019/196938 | A1 | 10/2009 | |
| WO | WO 2017/004383 | A1 | 1/2017 | |

OTHER PUBLICATIONS

Wang et al. Use of erlotinib and thalidomide in advanced NSCLC patients with acquired resistance to erlotinib: A pilot study Pathology—Research and Practice, 2018, 214, 2, 263-267 (Year: 2018).*
Pantani, G. et al. Bioisosterism: A Rational Approach in Drug Design. Chem. Rev. 1996, 96, 8, 3147-3176 (Year: 1996).*
Bhanumathy, K. et al. Protein Tyrosine Kinases: Their Roles and Their Targeting in Leukemia. Cancers 2021, 13(2), 184 (Year: 2021).*
Sigismund "Emerging functions of the EGFR in cancer" Mol Oncol. Nov. 27, 2017;12(1):3-20 (Year: 2017).*
Pan, P. et al. Mechanisms of EGFR Resistance in Glioblastoma. Int J Mol Sci. Nov. 11, 2020;21(22):8471 (Year: 2020).*
International Search Report and Written Opinion from the Korean Search Authority of the Korean Intellectual Property Office, in PCT/KR2020/016372, mailed on Feb. 26, 2021, 7 pages (with English translation of the International Search Report, 3 pages).
Sharma et al., "Epidermal growth factor receptor mutations in lung cancer," *Cancer* 7: 169-181, Mar. 2007.
Sun et al., "Structural modification of an EGFR inhibitor that showed weak off-target activity against RET leading to the discovery of a potent RET inhibitor," *Mol Divers.* 18: 403-409, 2014.

* cited by examiner

*Primary Examiner* — Clinton A Brooks
*Assistant Examiner* — Nicola Maria Bauer
(74) *Attorney, Agent, or Firm* — Klarquist Sparkman, LLP

(57) ABSTRACT

The present invention relates to a benzamide derivative, a preparation method therefor, and a pharmaceutical composition comprising same as an active ingredient for prevention or treatment of cancer. The benzamide derivative provided in an aspect of the present invention can be used for preventing or treating cancer by suppressing EGFR mutation, and exhibits a remarkable synergy effect on anticancer activity when administered in combination with an EGFR antagonist such as Cetuximab, thus finding advantageous uses as an anticancer agent.

16 Claims, 2 Drawing Sheets

BENZAMIDE DERIVATIVE, PREPARATION METHOD THEREFOR, AND PHARMACEUTICAL COMPOSITION COMPRISING SAME AS ACTIVE INGREDIENT FOR PREVENTION OR TREATMENT OF CANCER

CROSS REFERENCE TO RELATED APPLICATIONS

This is the U.S. National Stage of International Application No. PCT/KR2020/016372, filed Nov. 19, 2020, which in turn claims the benefit of priority under 35 U.S.C. § 119 from Korean Patent Application No. 10-2019-0148459, filed Nov. 19, 2019. The Korean patent application is incorporated herein in its entirety by reference.

BACKGROUND OF THE INVENTION

1. Field of the Invention

The present invention relates to a benzamide derivative, a preparation method therefor, and a pharmaceutical composition comprising the same as an active ingredient for the prevention or treatment of cancer.

2. Description of the Related Art

The incidence of cancer is related to various environmental factors including chemicals, radiation, and viruses, as well as changes in oncogenes, tumor suppressor genes, and genes related to apoptosis and DNA repair. Recent understanding of the molecular mechanisms of cancer has enabled targeted anticancer therapy, a new treatment.

Targeted agents are generally made to target the molecules that cancer cells characteristically have to show their effectiveness. Molecular targets are genes related to cancer cell signal transduction pathway, angiogenesis, matrix, cell cycle regulator, and apoptosis. Currently, ‘signal transduction pathway inhibitors’ including tyrosine kinase inhibitors and ‘angiogenesis inhibitors’ are used as important targeted agents in cancer treatment.

Protein tyrosine kinases have been known to play an important role in many malignant tumors. In particular, epidermal growth factor receptor (EGFR), a receptor tyrosine kinase of the erbB family, is abnormally activated in many epithelial cell tumors including non-small cell lung carcinoma (NSCLC), breast cancer, glioma, squamous cell carcinoma of the head and neck, colon cancer, rectal carcinoma, head and neck cancer, stomach cancer, and prostate cancer, and it has been known that the activation of the EGFR-tyrosine kinase causes continuous cell proliferation, invasion of surrounding tissues, distant metastasis, blood vessel formation, and increases cell survival.

Particularly, EGFR is one of the ErbB tyrosine kinase receptors family (EGFR, HER-2, ErbB-3, ErbB-4), and is a transmembrane tyrosine kinase having an intracellular domain including an extracellular ligand-binding domain and a tyrosine kinase domain. When a ligand is bound to a receptor that forms a homodimer or heterodimer, the intracellular tyrosine kinase is activated, and the signal stimulated by EGFR activates phosphatidylinositol 3-kinase (PI3K/AKT/mTOR, RAS/RAF/MAPK, JAK/STAT) signaling pathway (Non-Patent Reference 1, Nat Rev Cancer 2007; 7:169-81. Epidermal growth factor receptor mutations in lung cancer).

In particular, EGFR is overexpressed in more than half of non-small cell lung cancer (NSCLC), and many studies have been conducted with EGFR as a target of treatment. EGFR TKI (tyrosine kinase inhibitor), which inhibits EGFR tyrosine kinase activity, has been developed, and the representative drugs include gefitinib (IRESSA™), erlotinib (TARCEVA™), and lapatinib (TYKERB™, TYVERB™).

On the other hand, in 2004, it was reported that the activation mutation of EGFR is correlated with the response to gefitinib therapy in non-small-cell lung cancer (NSCLC). Particularly, the EGFR mutation is largely classified into a sensitizing mutation and a resistant mutation, and the deletion of exon 19 and the L858R point mutation of exon 21 are the most important sensitizing mutations, accounting for about 85-90%, and the exon 19 deletion mutation is known to have better sensitivity to TKI. On the other hand, the T790M point mutation of exon 20 is the most important resistant mutation and is known to be found in more than 50% of acquired resistance patients.

Somatic mutations identified so far include intraframe deletions in exon 19 or insertions in exon 20, as well as point mutations in which a single nucleic acid residue is modified in the expressed protein (e.g., L858R, G719S, G719C, G719A, and L861Q).

Despite the initial clinical effects of gefitinib/erlotinib on NSCLC patients with EGFR mutations, advanced cancer eventually develops in most patients during therapy with these agents. Early studies of relapsed specimens identified a secondary EGFR mutation, T790M, which makes zepithinib and erlotinib ineffective inhibitors of EGFR kinase activity. It was demonstrated in subsequent studies that the EGFR T790M mutation was found in approximately 50% (24/48) of tumors of patients who acquired resistance to gefitinib or erlotinib. This secondary genetic modification occurs at a position similar to the ‘gatekeeper’ residue and the secondary resistance allele associated with it in patients treated with kinase inhibitors (e.g., T315I in ABL in imatinib resistant CML).

It has long been known that the EGFR mutation, EGFR_del19 or EGFR_L858R, is the major cause of non-small cell lung cancer and head and neck cancer, and their therapeutic drugs, Iressa and Taseba, have been developed and are currently used in clinical trials. However, when these drugs were used in patients, acquired resistance was observed, resulting in EGFR secondary mutations based on the structure of the drug, and it was also found that this is the main cause of actual drug resistance. When the first generation EGFR inhibitors are used for an average of 10 months, the acquired resistance, the T790M mutation located in the gatekeeper of the EGFR kinase, occurs, and the first generation EGFR inhibitors are not effective. That is, EGFR_del19_T790M or EGFR_L858R_T790M double mutation occurs, and the conventional therapeutic agents do not show efficacy.

Based on these facts, the need for the development of $2^{nd}$ and $3^{rd}$ generation drugs with excellent drug efficacy and new structures emerged.

In the past 10 years, various $3^{rd}$ generation new drug candidates that have an effect on the double mutation of EGFR T790M have been discovered and clinical studies are in progress, and the most advanced of them is AZD9291 of AstraZeneca, a multinational pharmaceutical company. However, it has been reported that resistance to AZD9291 occurs in about 10 months, resulting in loss of the drug efficacy of AZD9291, and in particular, resistance to triple mutations including C797S has been reported.

Accordingly, there is a need for the development of inhibitors that exhibit relatively low inhibition against WT EGFR, and higher inhibition against specific activated or resistant mutant forms of EGFR.

SUMMARY OF THE INVENTION

It is an object of the present invention to provide a benzamide derivative capable of preventing or treating cancer by inhibiting EGFR mutation.

It is another object of the present invention to provide a pharmaceutical composition for the prevention or treatment of cancer comprising the benzamide derivative as an active ingredient.

It is another object of the present invention to provide a health functional food composition for the prevention or amelioration of cancer comprising the benzamide derivative as an active ingredient.

It is another object of the present invention to provide a combination preparation for the prevention or treatment of cancer comprising the benzamide derivative and an EGFR antagonist.

It is another object of the present invention to provide a benzamide derivative used to prepare a drug for the prevention or treatment of cancer.

It is another object of the present invention to provide a use of the benzamide derivative for the preparation of a drug for the prevention or treatment of cancer.

It is another object of the present invention to provide a method for preventing or treating cancer by administering the benzamide derivative.

To achieve the above objects, in one aspect of the present invention, the present invention provides a compound represented by formula 1 below, an optical isomer thereof, a solvate thereof, a hydrate thereof, or a pharmaceutically acceptable salt thereof.

[Formula 1]

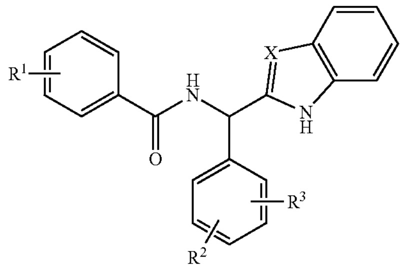

(In formula 1, $R^1$ is substituted $C_{6-12}$ aryl, wherein, the substituted $C_{6-12}$ aryl is $C_{6-12}$ aryl substituted with unsubstituted or substituted 5-10 membered heterocycloalkyl containing one or more heteroatoms selected from the group consisting of N, O and S, the substituted 5~10 membered heterocycloalkyl is $C_{1-15}$ straight or branched alkylcarbonyl, —$NR^4R^5$, or 5-10 membered heterocycloalkyl substituted with 5~7 membered heterocycloalkyl unsubstituted or substituted with one or more $C_{1-5}$ straight or branched alkyl containing one or more heteroatoms selected from the group consisting of N, O and S, and $R^4$ and $R^5$ are independently hydrogen or $C_{1-15}$ straight or branched alkyl;

$R^2$ is halogen;

$R^3$ is —OH, or $C_{1-15}$ straight or branched alkoxy; and

X is =CH—, or =N—).

In another aspect of the present invention, the present invention provides a pharmaceutical composition comprising a compound represented by formula 1, an optical isomer thereof, a solvate thereof, a hydrate thereof, or a pharmaceutically acceptable salt thereof as an active ingredient for the prevention or treatment of cancer.

In another aspect of the present invention, the present invention provides a health functional food composition comprising a compound represented by formula 1, an optical isomer thereof, a solvate thereof, a hydrate thereof, or a pharmaceutically acceptable salt thereof as an active ingredient for the prevention or amelioration of cancer.

In another aspect of the present invention, the present invention provides a combination preparation comprising a compound represented by formula 1, an optical isomer thereof, a solvate thereof, a hydrate thereof, or a pharmaceutically acceptable salt thereof; and an EGFR antagonist for the prevention or treatment of cancer.

In another aspect of the present invention, the present invention provides a benzamide derivative used to prepare a drug for the prevention or treatment of cancer.

In another aspect of the present invention, the present invention provides a use of the benzamide derivative for the preparation of a drug for the prevention or treatment of cancer.

In another aspect of the present invention, the present invention provides a method for preventing or treating cancer by administering the benzamide derivative.

Advantageous Effect

The benzamide derivative provided in an aspect of the present invention can be used for preventing or treating cancer by suppressing EGFR mutation, and exhibits a remarkable synergy effect on anticancer activity when administered in combination with an EGFR antagonist such as Cetuximab, so that it can be effectively used as an anticancer agent.

DESCRIPTION OF THE PREFERRED EMBODIMENTS

Figure 1:
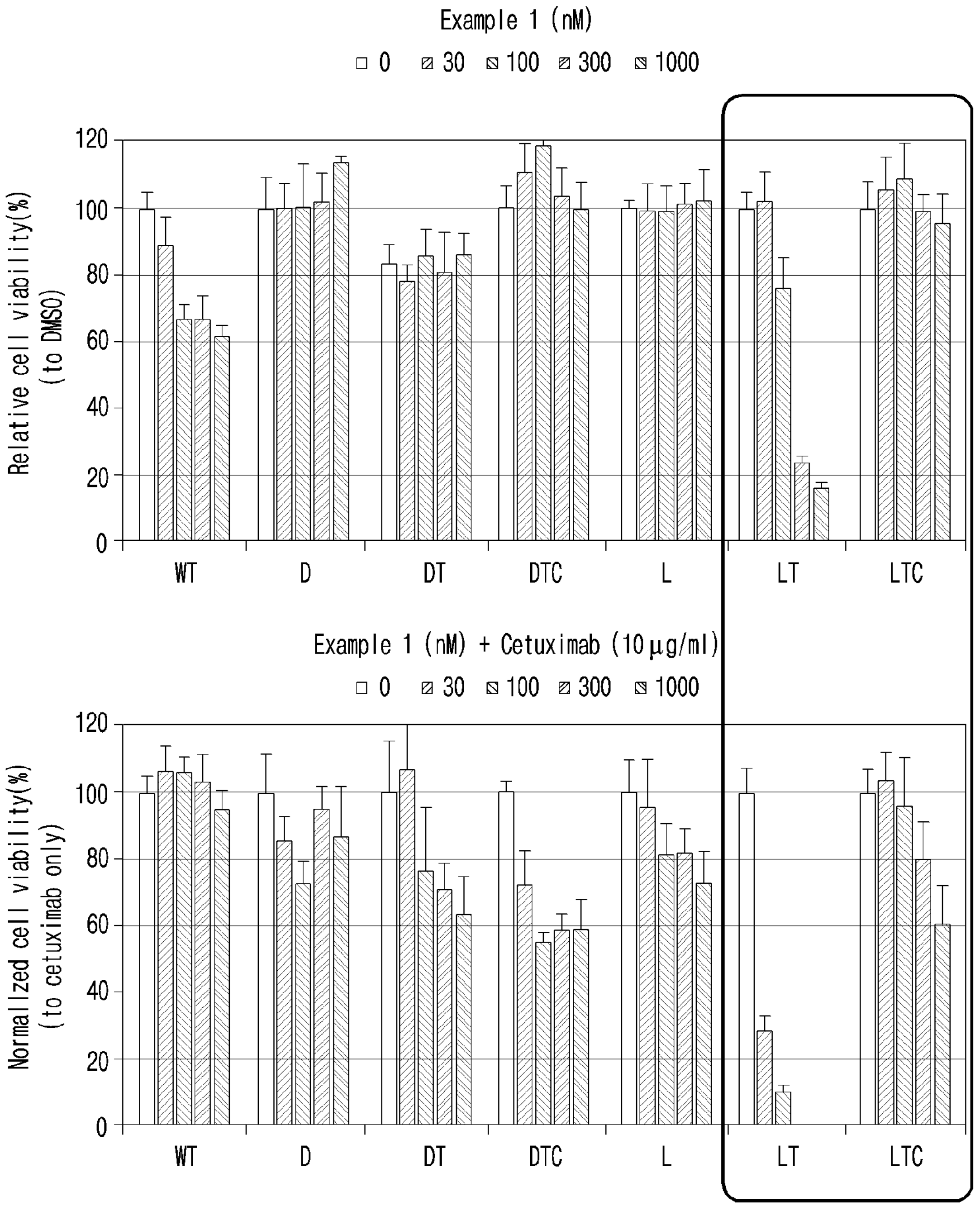
FIG. 1 and FIG. 2 are a graph showing the results of evaluating the anticancer activity when BaF3 cells overexpressing various EGFR mutations were treated with the example compound provided in one aspect of the present invention alone or in combination with cetuximab, known as an EGFR antagonist.

Hereinafter, the present invention is described in detail.

The embodiments of this invention can be modified in various other forms, and the scope of the present invention is not limited to the embodiments described below. It is well understood by those in the art who has the average knowledge on this field that the embodiments of the present invention are given to explain the present invention more precisely.

In addition, the "inclusion" of an element throughout the specification does not exclude other elements, but may include other elements, unless specifically stated otherwise.

In one aspect of the present invention, the present invention provides a compound represented by formula 1 below, an optical isomer thereof, a solvate thereof, a hydrate thereof, or a pharmaceutically acceptable salt thereof.

[Formula 1]

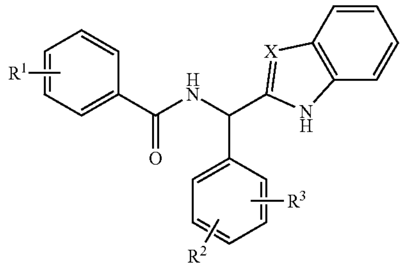

(In formula 1, $R^1$ is substituted $C_{6-12}$ aryl, wherein, the substituted $C_{6-12}$ aryl is $C_{6-12}$ aryl substituted with unsubstituted or substituted 5~10 membered heterocycloalkyl containing one or more heteroatoms selected from the group consisting of N, O and S, the substituted 5~10 membered heterocycloalkyl is $C_{1-15}$ straight or branched alkylcarbonyl, —$NR^4R^5$, or 5-10 membered heterocycloalkyl substituted with 5~7 membered heterocycloalkyl unsubstituted or substituted with one or more $C_{1-5}$ straight or branched alkyl containing one or more heteroatoms selected from the group consisting of N, O and S, and $R^4$ and $R^5$ are independently hydrogen or $C_{1-15}$ straight or branched alkyl;

$R^2$ is halogen;

$R^3$ is —OH, or $C_{1-15}$ straight or branched alkoxy; and

X is =CH—, or =N—).

In another aspect, $R^1$ is substituted $C_{6-12}$ aryl, wherein, the substituted $C_{6-12}$ aryl is $C_{6-12}$ aryl substituted with unsubstituted or substituted 5~10 membered heterocycloalkyl containing one or more heteroatoms selected from the group consisting of N, O and S, the substituted 5~10 membered heterocycloalkyl is $C_{1-10}$ straight or branched alkylcarbonyl, —$NR^4R^5$, or 5-10 membered heterocycloalkyl substituted with 6 membered heterocycloalkyl unsubstituted or substituted with one or more $C_{1-3}$ straight or branched alkyl containing one or more heteroatoms selected from the group consisting of N, O and S, and $R^4$ and $R^5$ are independently hydrogen or $C_{1-10}$ straight or branched alkyl;

$R^2$ is halogen;

$R^3$ is —OH, or $C_{1-10}$ straight or branched alkoxy; and

X is =CH—, or =N—.

In another aspect, $R^1$ is

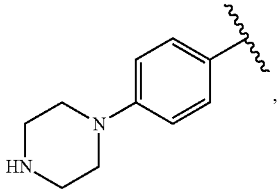

,

-continued

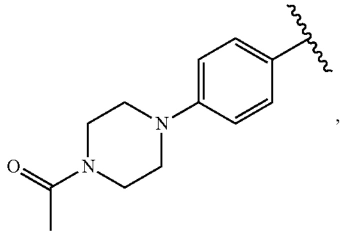

,

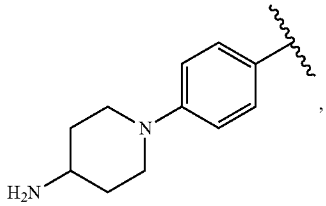

,

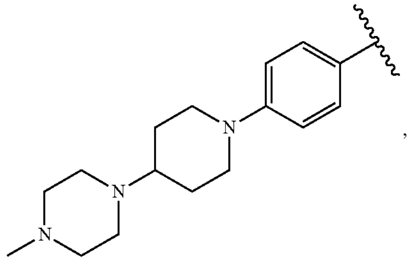

,

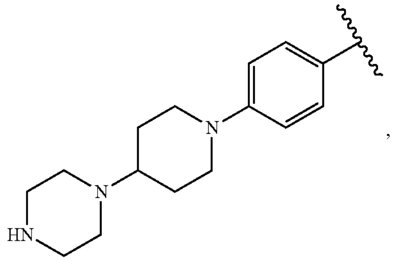

,

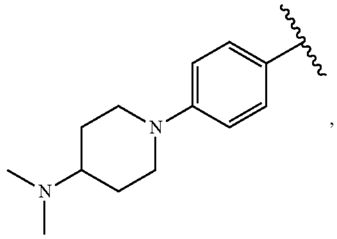

,

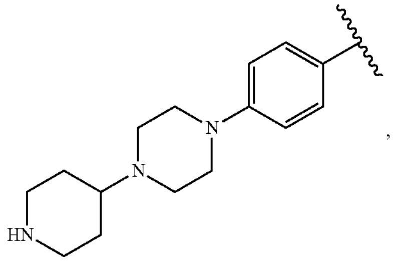

,

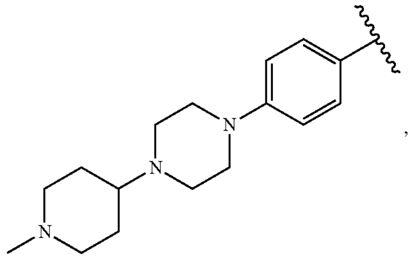

,

-continued

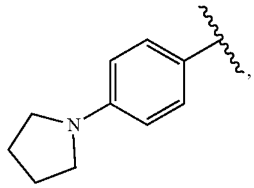

,

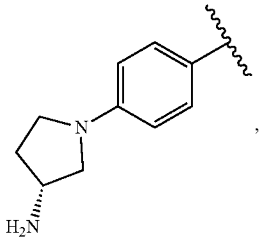

, or

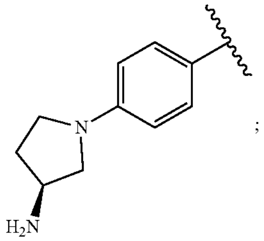

;

$R^2$ is —F, or —Cl;

$R^3$ is —OH; and

X is =CH—.

In another aspect, the compound represented by formula 1 can be a compound represented by formula 2 below.

[Formula 2]

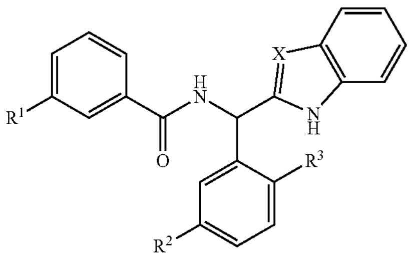

In formula 2, $R^1$, $R^2$, $R^3$ and X are independently as defined in Formula 1 above.

In another aspect, the compound represented by formula 1 is preferably any one selected from the group consisting of the following compounds.

(1) (R)—N-((5-fluoro-2-hydroxyphenyl)(1H-indole-2-yl)methyl)-4'-(piperazine-1-yl)-[1,1'-biphenyl]-3-carboxamide;

(2) (R)-4'-(4-acetylpiperazine-1-yl)-N-((5-fluoro-2-hydroxyphenyl)(1H-indole-2-yl)methyl)-[1,1'-biphenyl]-3-carboxamide;

(3) (R)-4'-(4-aminopiperidine-1-yl)-N-((5-fluoro-2-hydroxyphenyl)(1H-indole-2-yl)methyl)-[1,1'-biphenyl]-3-carboxamide;

(4) (R)-4'-(4-aminopiperidine-1-yl)-N-((5-chloro-2-hydroxyphenyl)(1H-indole-2-yl)methyl)-[1,1'-biphenyl]-3-carboxamide;

(5) (R)—N-((5-fluoro-2-hydroxyphenyl)(1H-indole-2-yl)methyl)-4'-(4-(4-methylpiperazine-1-yl)piperidine-1-yl)-[1,1'-biphenyl]-3-carboxamide;

(6) (R)—N-((5-fluoro-2-hydroxyphenyl)(1H-indole-2-yl)methyl)-4'-(4-(piperazine-1-yl)piperidine-1-yl)-[1,1'-biphenyl]-3-carboxamide;

(7) (R)-4'-(4-(dimethylamino)piperidine-1-yl)-N-((5-fluoro-2-hydroxyphenyl)(1H-indole-2-yl)methyl)-[1,1'-biphenyl]-3-carboxamide;

(8) (R)—N-((5-fluoro-2-hydroxyphenyl)(1H-indole-2-yl)methyl)-4'-(4-(piperidine-4-yl)piperazine-1-yl)-[1,1'-biphenyl]-3-carboxamide;

(9) (R)—N-((5-fluoro-2-hydroxyphenyl)(1H-indole-2-yl)methyl)-4'-(4-(1-methylpiperidine-4-yl)piperazine-1-yl)-[1,1'-biphenyl]-3-carboxamide;

(10) (R)—N-((5-fluoro-2-hydroxyphenyl)(1H-indole-2-yl)methyl)-4'-(pyrrolidine-1-yl)-[1,1'-biphenyl]-3-carboxamide;

(11) 4'-((R)-3-aminopyrrolidine-1-yl)-N—((R)-(5-fluoro-2-hydroxyphenyl)(1H-indole-2-yl)methyl)-[1,1'-biphenyl]-3-carboxamide;

(12) 4'-((S)-3-aminopyrrolidine-1-yl)-N—((R)-(5-fluoro-2-hydroxyphenyl)(1H-indole-2-yl)methyl)-[1,1'-biphenyl]-3-carboxamide; and

(13) 4'-((S)-3-aminopyrrolidine-1-yl)-N—((R)-(5-chloro-2-hydroxyphenyl)(1H-indole-2-yl)methyl)-[1,1'-biphenyl]-3-carboxamide.

The compound represented by formula 1 of the present invention can be used as a form of a pharmaceutically acceptable salt, in which the salt is preferably acid addition salt formed by pharmaceutically acceptable free acids. The acid addition salt herein can be obtained from inorganic acids such as hydrochloric acid, nitric acid, phosphoric acid, sulfuric acid, hydrobromic acid, hydroiodic acid, nitrous acid, and phosphorous acid; non-toxic organic acids such as aliphatic mono/dicarboxylate, phenyl-substituted alkanoate, hydroxy alkanoate, alkandioate, aromatic acids, and aliphatic/aromatic sulfonic acids; or organic acids such as acetic acid, benzoic acid, citric acid, lactic acid, maleic acid, gluconic acid, methanesulfonic acid, 4-toluenesulfonic acid, tartaric acid, and fumaric acid. The pharmaceutically non-toxic salts are exemplified by sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutylate, caprate, heptanoate, propiolate, oxalate, malonate, succinate, suberate, cabacate, fumarate, maliate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, hydroxybutylate, glycolate, malate, tartrate, methanesulfonate, propanesulfonate, naphthalene-1-sulfonate, naphthalene-2-sulfonate, and mandelate.

The acid addition salt according to the present invention can be prepared by the conventional method known to those in the art. For example, the derivative represented by formula 1 is dissolved in an organic solvent such as methanol, ethanol, acetone, methylenechloride, and acetonitrile, to which organic acid or inorganic acid is added to induce precipitation. Then, the precipitate is filtered and dried to give the salt. Or the solvent and the excessive acid are distillated under reduced pressure, and dried to give the salt. Or the precipitate is crystallized in an organic solvent to give the same.

A pharmaceutically acceptable metal salt can be prepared by using a base. Alkali metal or alkali earth metal salt is obtained by the following processes: dissolving the compound in excessive alkali metal hydroxide or alkali earth metal hydroxide solution; filtering non-soluble compound salt; evaporating the remaining solution and drying thereof. At this time, the metal salt is preferably prepared in the pharmaceutically suitable form of sodium, potassium, or calcium salt. And the corresponding silver salt is prepared by the reaction of alkali metal or alkali earth metal salt with proper silver salt (ex; silver nitrate).

In addition, the present invention includes not only the compound represented by formula 1 but also a pharmaceutically acceptable salt thereof, and a solvate, an optical isomer, or a hydrate possibly produced from the same.

The term "hydrate" refers to a compound or a salt thereof of the present invention containing a stoichiometric or non-stoichiometric amount of water bound by a non-covalent intermolecular force. The hydrate of the compound represented by formula 1 of the present invention can contain a stoichiometric or non-stoichiometric amount of water bonded by a non-covalent intermolecular force. The hydrate can contain 1 equivalent or more of water, preferably 1 to 5 equivalents of water. The hydrate can be prepared by crystallizing the compound represented by formula 1, the isomer thereof, or the pharmaceutically acceptable salt thereof from water or the solvent containing water.

The term "solvate" refers to a compound or a salt thereof of the present invention containing a stoichiometric or non-stoichiometric amount of solvent bound by a non-covalent intermolecular force. Preferred solvents therefor include volatile, non-toxic, and/or solvents suitable for administration to human.

The term "isomer" refers to a compound or a salt thereof of the present invention having the same chemical formula or molecular formula, but structurally or sterically different. Such isomers include structural isomers such as tautomers, R or S isomers having an asymmetric carbon center, stereoisomers such as geometric isomers (trans, cis), and optical isomers (enantiomers). All these isomers and mixtures thereof are also included in the scope of the present invention.

The compound represented by formula 1 can be prepared by the following general formulas, and representatively, general formulas 1 to 3 corresponding to the preparation process of the compound of Example 1 are shown below.

Scheme 1.

General Formula 1

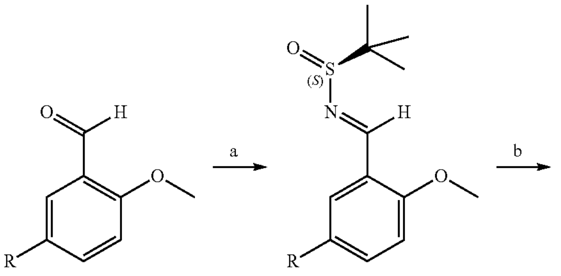

R = F, Cl

-continued

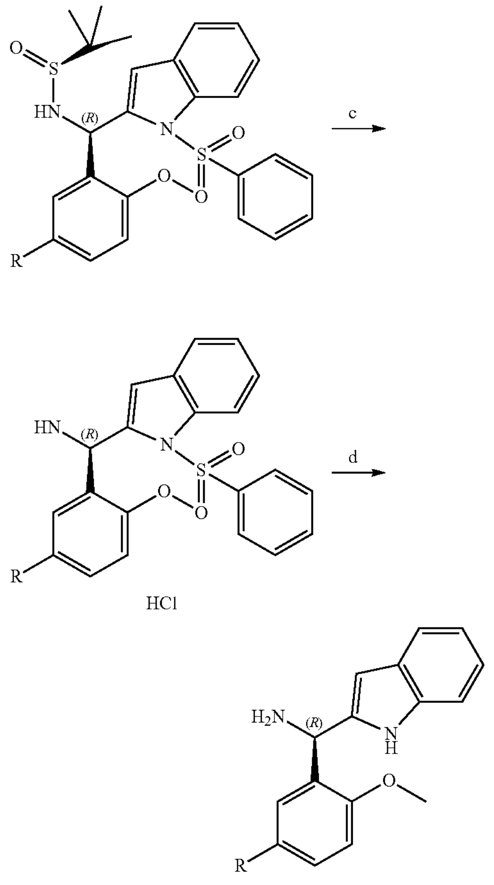

Reagents and conditions: (a) (S)-2-methylpropane-2-sulfinamide, titanium (IV) ethoxide, THF, rt, 17 h; (b) 1-(phenylsulfonyl)-1H-indole, n-BuLi, THF, -75° C. to rt, 4 h; (c) 4N HCl dissolved in dioxane, MeOH, rt, 1 h; (d) 5N NaOH, MeOH, reflux, overnight.

Scheme 2.

General Formula 2

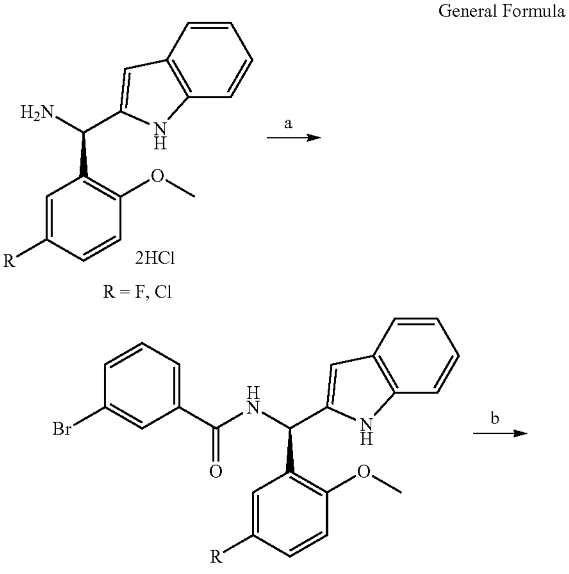

-continued

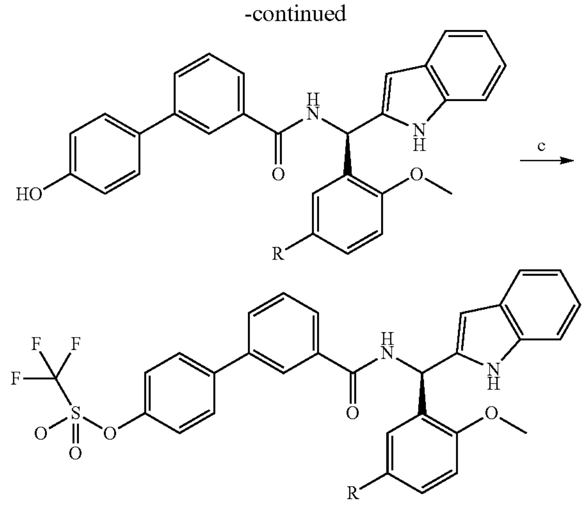

Reagents and conditions:
(a) 3-bromobenzoic acid, 1-ethyl-3-(3-dimethylaminopropyl)carbodiimide, hydroxybenzotriazole, triethylamine, $CH_2Cl_2$, rt, overnight;
(b) 4-(4,4,5,5-tetramethyl-1,3,2-dioxaborolene-2-yl)phenol, $Pd(OAc)_2$, Sphos, $Na_2CO_3$, dioxane/$H_2O$, 100° C., overnight;
(c) 1,1,1-trifluoro-N-phenyl-N-((trifluoromethyl)sulfonyl) methanesulfonamide, triethylamine, 4-dimethylaminopyridine, $CH_2Cl_2$, rt, 3 h.

Scheme 3.

General Formula 3

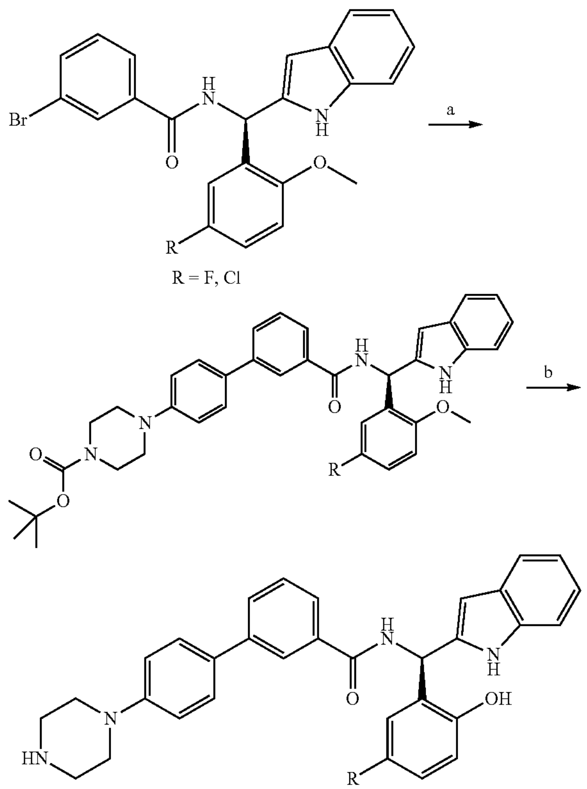

Reagents and conditions:
(a) tert-butyl 4-(4-(4,4,5,5-tetramethyl-1,3,2-dioxaborolene-2-yl) piperazine-1-carboxylate, $Pd(OAc)_2$, Sphos, $Na_2CO_3$, dioxane/$H_2O$, 100° C., overnight;
(b) 1 M $BBr_3$ dissolved in $CH_2Cl_2$, -78° C. to rt, overnight.

In another aspect of the present invention, the present invention provides a pharmaceutical composition comprising a compound represented by formula 1, an optical isomer thereof, a solvate thereof, a hydrate thereof, or a pharmaceutically acceptable salt thereof as an active ingredient for the prevention or treatment of cancer.

At this time, the compound may prevent or treat cancer by inhibiting EGFR (epidermal growth factor receptor) mutation, and the EGFR (epidermal growth factor receptor) mutation can be at least one selected from the group consisting of EGFR L858R/T790M and EGFR L858R/T790M/C797S.

The cancer can be at least one selected from the group consisting of pseudomyxoma, intrahepatic biliary tract cancer, hepatoblastoma, liver cancer, thyroid cancer, colon cancer, testis cancer, myelodysplastic syndrome, glioblastoma, oral cancer, lip cancer, mycelia, acute myelogenous leukemia, acute lymphocytic leukemia, basal cell cancer, ovarian epithelial carcinoma, ovarian germ cell cancer, male breast cancer, brain cancer, pituitary adenoma, multiple myeloma, gallbladder cancer, biliary tract cancer, colorectal cancer, chronic myelogenous leukemia, chronic lymphocytic leukemia, retinoblastoma, choroidal melanoma, ampullar of vater cancer, bladder cancer, peritoneal cancer, parathyroid cancer, adrenal cancer, nasal cavity cancer, non-small cell lung cancer, tongue cancer, astrocytoma, small cell lung cancer, pediatric brain cancer, pediatric lymphoma, pediatric leukemia, small intestine cancer, meningioma, esophageal cancer, glioma, renal pelvic cancer, renal cell carcinoma, heart cancer, duodenal cancer, malignant soft tissue cancer, malignant bone cancer, malignant lymphoma, malignant mesothelioma, malignant melanoma, eye cancer, vulvar cancer, ureteral cancer, urethral cancer, primary site unknown cancer, gastric lymphoma, stomach cancer, gastric carcinoid tumor, gastrointestinal stromal tumor, Wilms cancer, breast cancer, sarcoma, penile cancer, pharyngeal cancer, gestational trophoblastic disease, cervical cancer, endometrial cancer, uterine sarcoma, prostate cancer, metastatic bone cancer, metastatic brain cancer, mediastinal cancer, rectal cancer, rectal carcinoma, vaginal cancer, spinal cord cancer, acoustic tumor, pancreatic cancer, salivary gland cancer, Kaposi's sarcoma, Paget's disease, tonsil cancer, squamous cell carcinoma, lung adenocarcinoma, lung cancer, lung squamous cell carcinoma, skin cancer, anal cancer, rhabdomyosarcoma, laryngeal cancer, pleura cancer and thymus cancer.

The compound represented by formula 1 of the present invention or the pharmaceutically acceptable salt thereof can be administered orally or parenterally and be used in general forms of pharmaceutical formulation. That is, the compound or the pharmaceutically acceptable salt thereof can be prepared for oral or parenteral administration by mixing with generally used diluents or excipients such as fillers, extenders, binders, wetting agents, disintegrating agents and surfactants. Solid formulations for oral administration are tablets, pills, powders, granules and capsules. These solid formulations are prepared by mixing one or more compounds with one or more suitable excipients such as starch, calcium carbonate, sucrose or lactose, gelatin, etc. Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions, and emulsions. Water insoluble excipients and suspensions can contain, in addition to the active compound or compounds, propylene glycol, polyethylene glycol, vegetable oil like olive oil, injectable ester like ethylolate, etc.

The pharmaceutical composition comprising the compound represented by formula 1 or the pharmaceutically acceptable salt thereof as an active ingredient can be administered by parenterally and the parenteral administration includes subcutaneous injection, intravenous injection, intramuscular injection, or intrathoracic injection.

At this time, to prepare the compound represented by formula 1 or the pharmaceutically acceptable salt thereof as a formulation for parenteral administration, the compound represented by formula 1 or the pharmaceutically acceptable salt thereof is mixed with a stabilizer or a buffering agent in water to produce a solution or suspension, which is then formulated as ampoules or vials. The composition herein can be sterilized and additionally contains preservatives, stabilizers, wettable powders or emulsifiers, salts and/or buffers for the regulation of osmotic pressure, and other therapeutically useful materials, and the composition can be formulated by the conventional mixing, granulating or coating method.

The formulations for oral administration are exemplified by tablets, pills, hard/soft capsules, solutions, suspensions, emulsions, syrups, granules, elixirs, and troches, etc. These formulations can include diluents (for example, lactose, dextrose, sucrose, mannitol, sorbitol, cellulose, and/or glycine) and lubricants (for example, silica, talc, stearate and its magnesium or calcium salt, and/or polyethylene glycol) in addition to the active ingredient. Tablets can include binding agents such as magnesium aluminum silicate, starch paste, gelatin, methylcellulose, sodium carboxymethylcellulose and/or polyvinylpyrolidone, and if necessary can additionally include disintegrating agents such as starch, agarose, alginic acid or its sodium salt or azeotropic mixtures and/or absorbents, coloring agents, flavours, and sweeteners.

In another aspect of the present invention, the present invention provides a health functional food composition comprising a compound represented by formula 1, an optical isomer thereof, a solvate thereof, a hydrate thereof, or a pharmaceutically acceptable salt thereof as an active ingredient for the prevention or amelioration of cancer.

The compound represented by formula 1 of the present invention can be added as it is or as mixed with other food components according to the conventional method. The mixing ratio of active ingredients can be regulated according to the purpose of use (prevention or amelioration). In general, the compound of the present invention is preferably added to food or beverages by 0.1~90 weight part for the total weight of the food. However, if long term administration is required for health and hygiene or regulating health condition, the content can be lower than the above but higher content can be accepted as well since the compound of the present invention has been proved to be very safe.

In addition, the health beverage composition of the present invention can additionally include various flavors or natural carbohydrates, etc, like other beverages. The natural carbohydrates above can be one of monosaccharides such as glucose and fructose; disaccharides such as maltose and sucrose; polysaccharides such as dextrin and cyclodextrin, and sugar alcohols such as xilytole, sorbitol and erythritol. Besides, natural sweetening agents (thaumatin, stevia extract, for example rebaudioside A, glycyrrhizin, etc.) and synthetic sweetening agents (saccharin, aspartame, etc.) can be included as a sweetening agent. The content of the natural carbohydrate is preferably 1~20 g and more preferably 5~12 g in 100 g of the composition of the present invention.

In addition to the ingredients mentioned above, the compound represented by formula 1 of the present invention can include in variety of nutrients, vitamins, minerals (electrolytes), flavors including natural flavors and synthetic flavors, coloring agents and extenders (cheese, chocolate, etc.), pectic acid and its salts, alginic acid and its salts, organic acid, protective colloidal viscosifiers, pH regulators, stabilizers, antiseptics, glycerin, alcohols, carbonators which used to be added to soda, etc. In addition, the compound represented by formula 1 of the present invention can contain natural fruit juice and fruit flesh for the production of fruit juice beverages and vegetable beverages.

The cancer can be at least one selected from the group consisting of pseudomyxoma, intrahepatic biliary tract cancer, hepatoblastoma, liver cancer, thyroid cancer, colon cancer, testis cancer, myelodysplastic syndrome, glioblastoma, oral cancer, lip cancer, mycelia, acute myelogenous leukemia, acute lymphocytic leukemia, basal cell cancer, ovarian epithelial carcinoma, ovarian germ cell cancer, male breast cancer, brain cancer, pituitary adenoma, multiple myeloma, gallbladder cancer, biliary tract cancer, colorectal cancer, chronic myelogenous leukemia, chronic lymphocytic leukemia, retinoblastoma, choroidal melanoma, ampullar of vater cancer, bladder cancer, peritoneal cancer, parathyroid cancer, adrenal cancer, nasal cavity cancer, non-small cell lung cancer, tongue cancer, astrocytoma, small cell lung cancer, pediatric brain cancer, pediatric lymphoma, pediatric leukemia, small intestine cancer, meningioma, esophageal cancer, glioma, renal pelvic cancer, renal cell carcinoma, heart cancer, duodenal cancer, malignant soft tissue cancer, malignant bone cancer, malignant lymphoma, malignant mesothelioma, malignant melanoma, eye cancer, vulvar cancer, ureteral cancer, urethral cancer, primary site unknown cancer, gastric lymphoma, stomach cancer, gastric carcinoid tumor, gastrointestinal stromal tumor, Wilms cancer, breast cancer, sarcoma, penile cancer, pharyngeal cancer, gestational trophoblastic disease, cervical cancer, endometrial cancer, uterine sarcoma, prostate cancer, metastatic bone cancer, metastatic brain cancer, mediastinal cancer, rectal cancer, rectal carcinoma, vaginal cancer, spinal cord cancer, acoustic tumor, pancreatic cancer, salivary gland cancer, Kaposi's sarcoma, Paget's disease, tonsil cancer, squamous cell carcinoma, lung adenocarcinoma, lung cancer, lung squamous cell carcinoma, skin cancer, anal cancer, rhabdomyosarcoma, laryngeal cancer, pleura cancer and thymus cancer.

In another aspect of the present invention, the present invention provides a combination preparation comprising a compound represented by formula 1, an optical isomer thereof, a solvate thereof, a hydrate thereof, or a pharmaceutically acceptable salt thereof; and an EGFR antagonist for the prevention or treatment of cancer.

At this time, the EGFR antagonist can be at least one selected from the group consisting of Cetuximab, Erlotinib, Gefitinib, and Panitumumab.

In another aspect of the present invention, the present invention provides a method for treating cancer, which comprises a step of administering a pharmaceutical composition or a health functional food composition comprising a compound represented by formula 1, an optical isomer thereof, a solvate thereof, a hydrate thereof, or a pharmaceutically acceptable salt thereof as an active ingredient to a subject in need.

In another aspect of the present invention, the present invention provides a compound represented by formula 1, an optical isomer thereof, a solvate thereof, a hydrate thereof, or a pharmaceutically acceptable salt thereof for use in the prevention or treatment of cancer.

In another aspect of the present invention, the present invention provides a use of a compound represented by formula 1, an optical isomer thereof, a solvate thereof, a hydrate thereof, or a pharmaceutically acceptable salt thereof for the preparation of a drug for the prevention or treatment of cancer.

The benzamide derivative provided in an aspect of the present invention can be used for preventing or treating cancer by suppressing EGFR mutation, and exhibits a remarkable synergy effect on anticancer activity when administered in combination with an EGFR antagonist such as Cetuximab, so that it can be effectively used as an anticancer agent. The above is supported by the Examples and Experimental Examples described later.

Hereinafter, the present invention will be described in detail by the following examples and experimental examples.

However, the following examples and experimental examples are only for illustrating the present invention, and the contents of the present invention are not limited thereto.

Scheme 1.

General Formula 1

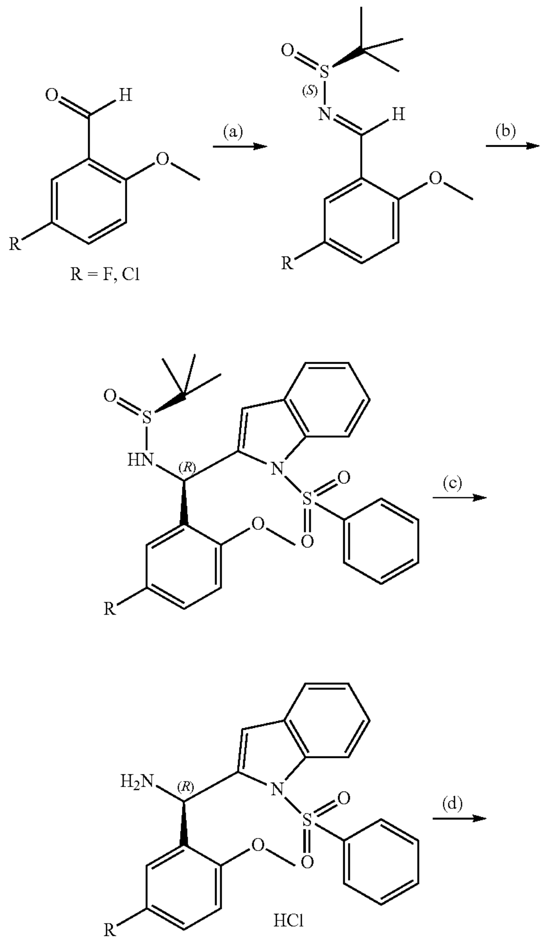

-continued

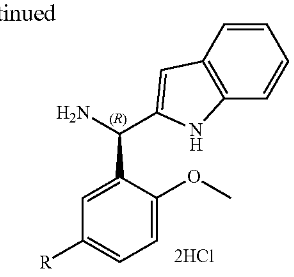

Reagents and conditions:
(a) (S)-2-methylpropane-2-sulfinamide, titanium (IV) ethoxide, THF, rt, 17 h;
(b) 1-(phenylsulfonyl)-1H-indole, n-BuLi, THF, -75° C. to rt, 4 h;
(c) 4 N HCl dissolved in dioxane, MeOH, rt, 1 h;
(d) 5 N NaOH, MeOH, reflux, overnight.

Preparative Example 1: Preparation of (S,E)-N-(5-fluoro-2-methoxybenzylidene)-2-methylpropane-2-sulfinamide

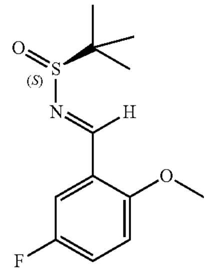

A mixture of 5-fluoro-2-methoxybenzaldehyde (100 mg, 0.73 mmol) and (S)-2-methylpropane-2-sulfinamide (88.5 mg, 0.73 mmol) and titanium(IV) ethoxide (331 mg, 1.45 mmol) were dissolved together in tetrahydrofuran (4 mL). The reaction flask was sealed with a septum, and the reaction mixture was stirred at room temperature for 17 hours. The reaction mixture was extracted with ethyl acetate and water. The ethyl acetate layer was collected, dried over anhydrous magnesium sulfate and filtered, and the solvent was removed by evaporation under reduced pressure to give (S,E)-N-(5-fluoro-2-methoxybenzylidene)-2-methylpropane-2-sulfinamide (157 mg).

90% yield: $^1$H NMR (500 MHz, chloroform-d) δ 9.03 (d, J=2.4 Hz, 1H), 7.69 (dd, J=8.8, 3.2 Hz, 1H), 7.19 (ddd, J=9.1, 7.7, 3.2 Hz, 1H), 6.94 (dd, J=9.1, 4.1 Hz, 1H), 3.90 (s, 3H), 1.29 (s, 9H).

Preparative Example 2: Preparation of (S,E)-N-(5-chloro-2-methoxybenzylidene)-2-methylpropane-2-sulfinamide

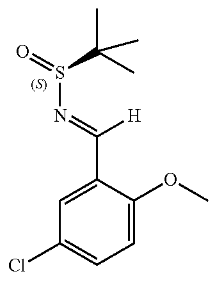

(S,E)-N-(5-chloro-2-methoxybenzylidene)-2-methylpropane-2-sulfinamide [Preparative Example 2] (90%) was prepared by a method similar to the method described in [Preparative Example 1].

$^1$H NMR (500 MHz, chloroform-d) δ 9.01 (s, 1H), 7.96 (d, J=2.7 Hz, 1H), 7.43 (dd, J=8.9, 2.7 Hz, 1H), 6.93 (d, J=8.9 Hz, 1H), 3.91 (s, 3H), 1.29 (s, 9H).

Preparative Example 3: Preparation of (S)—N—((R)-(5-fluoro-2-methoxyphenyl)(1-(phenylsulfonyl)-1H-indole-2-yl)methyl)-2-methylpropane-2-sulfinamide

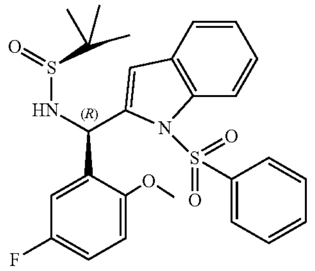

At −78° C., n-butyl lithium was added dropwise to a solution of 1-(phenylsulfonyl)-1H-indole (100 mg, 0.29 mmol) dissolved in tetrahydrofuran (4 mL). After reacting at −78° C. for 1 hour, a solution of (S,E)-N-(5-fluoro-2-methoxybenzylidene)-2-methylpropane-2-sulfinamide [Preparative Example 1] (33.5 mg, 0.09 mmol) dissolved in THF was added thereto, and the mixture was stirred at −78° C. for 2 hours. The reaction was terminated by adding a saturated $NH_4Cl$ aqueous solution to the mixture, followed by extraction with ethyl acetate. The ethyl acetate layer was collected, dried over anhydrous magnesium sulfate and filtered. The solvent was removed by evaporation under reduced pressure. The residue was purified by flash column chromatography ($CH_2Cl_2$/EtOAc, 10:1) filled with silica gel to give (S)—N—((R)-(5-fluoro-2-methoxyphenyl)(1-(phenylsulfonyl)-1H-indole-2-yl)methyl)-2-methylpropane-2-sulfinamide [Preparative Example 3] (38 mg, 75%) as a white solid.

$^1$H NMR (300 MHz, chloroform-d) δ 8.15 (dd, J=8.3, 1.1 Hz, 1H), 7.76-7.69 (m, 2H), 7.53-7.47 (m, 2H), 7.42-7.30 (m, 3H), 6.98 (ddd, J=8.9, 7.7, 3.0 Hz, 1H), 6.90 (dd, J=9.0, 4.5 Hz, 1H), 6.80 (d, J=5.8 Hz, 1H), 6.76 (d, J=0.9 Hz, 1H), 6.72 (dd, J=9.1, 3.0 Hz, 1H), 3.92 (s, 3H), 1.26 (s, 9H).

Preparative Example 4: Preparation of (S)—N—((R)-(5-chloro-2-methoxyphenyl)(1-(phenylsulfonyl)-1H-indole-2-yl)methyl)-2-methylpropane-2-sulfinamide

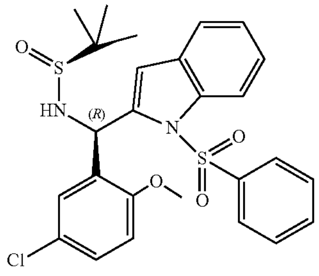

(S)—N—((R)-(5-chloro-2-methoxyphenyl)(1-(phenylsulfonyl)-1H-indole-2-yl)methyl)-2-methylpropane-2-sulfinamide [Preparative Example 4] (96%) was prepared by a method similar to the method described in [Preparative Example 3].

Preparative Example 5: Preparation of (R)-(5-fluoro-2-methoxyphenyl)(1-(phenylsulfonyl)-1H-indole-2-yl)methaneamine

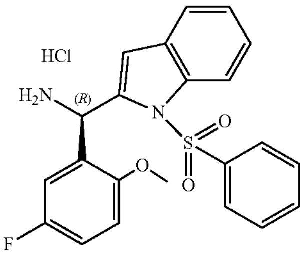

At room temperature, 4 N HCl dissolved in dioxane (0.16 mL, 0.32 mmol) was added to a solution of (S)—N—((R)-(5-fluoro-2-methoxyphenyl)(1-(phenylsulfonyl)-1H-indole-2-yl)methyl)-2-methylpropane-2-sulfinamide [Preparative Example 3] (80 mg, 0.16 mmol) dissolved in methanol (2 mL). The mixture was concentrated under reduced pressure. The residue was solidified with diethyl ether and filtered to give (R)-(5-fluoro-2-methoxyphenyl)(1-(phenylsulfonyl)-1H-indole-2-yl)methaneamine [Preparative Example 5] as a pink solid (yield: 84%).

$^1$H NMR (300 MHz, chloroform-d) δ 9.69-9.40 (m, 3H), 7.96 (d, J=8.5 Hz, 1H), 7.79 (d, J=7.7 Hz, 2H), 7.58 (s, 1H), 7.26-7.12 (m, 3H), 7.07-6.91 (m, 2H), 6.83 (dd, J=9.1, 4.2 Hz, 1H), 6.71 (s, 1H), 6.57 (d, J=8.5 Hz, 1H), 6.35 (s, 1H), 3.92 (s, 3H).

Preparative Example 6: Preparation of (R)-(5-chloro-2-methoxyphenyl)(1-(phenylsulfonyl)-1H-indole-2-yl)methaneamine

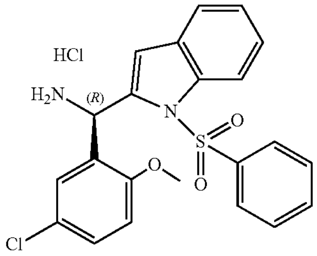

(R)-(5-chloro-2-methoxyphenyl)(1-(phenylsulfonyl)-1H-indole-2-yl)methaneamine [Preparative Example 6] (80%) was prepared by a method similar to the method described in [Preparative Example 5].

$^1$H NMR (300 MHz, methanol-$d_4$) δ 8.20 (dt, J=8.5, 0.9 Hz, 1H), 7.77-7.70 (m, 2H), 7.64-7.58 (m, 2H), 7.51-7.41 (m, 5H), 7.33 (td, J=7.6, 1.0 Hz, 1H), 7.21 (d, J=8.9 Hz, 1H), 7.13 (d, J=2.6 Hz, 1H), 6.81 (t, J=0.9 Hz, 1H), 6.71 (s, 1H), 3.95 (s, 3H).

Preparative Example 7: Preparation of (R)-(5-fluoro-2-methoxyphenyl)(1H-indole-2-yl)methaneamine

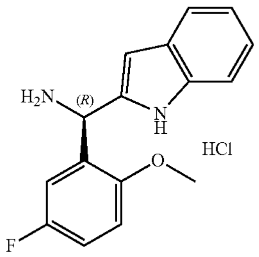

NaOH (5 mL, 20 mmol) dissolved in water was added to a solution of (R)-(5-fluoro-2-methoxyphenyl)(1-(phenylsulfonyl)-1H-indole-2-yl)methaneamine [Preparative Example 5] (1100 mg, 2.16 mmol) dissolved in methanol (11 mL), and the mixture was refluxed overnight. The mixture was concentrated under reduced pressure. The residue was solidified with 4N HCl dissolved in dioxane and ethyl acetate (1:1) to give (R)-(5-fluoro-2-methoxyphenyl)(1H-indole-2-yl)methaneamine [Preparative Example 7] as a yellow solid (yield: 62%).

$^1$H NMR (300 MHz, methanol-$d_4$) δ 7.59 (dt, J=7.8, 1.1 Hz, 1H), 7.40-7.35 (m, 1H), 7.26-7.13 (m, 3H), 7.07 (ddd, J=8.1, 7.1, 1.1 Hz, 1H), 6.99 (dd, J=8.9, 2.7 Hz, 1H), 6.62 (t, J=0.9 Hz, 1H), 6.01 (s, 1H), 3.97 (s, 3H), 3.68 (s, 3H).

Preparative Example 8: Preparation of (R)-(5-chloro-2-methoxyphenyl)(1H-indole-2-yl)methaneamine

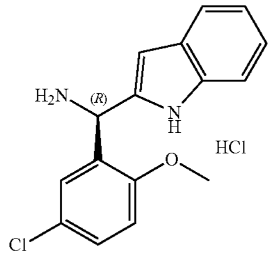

(R)-(5-chloro-2-methoxyphenyl)(1H-indole-2-yl)methaneamine (S,E)-N-(5-chloro-2-methoxybenzylidene)-2-methylpropane-2-sulfinamide [Preparative Example 8] (60%) was prepared by a method similar to the method described in [Preparative Example 7].

$^1$H NMR (300 MHz, methanol-$d_4$) δ 7.58 (d, J=7.8 Hz, 1H), 7.43 (dd, J=8.8, 2.6 Hz, 1H), 7.37 (dd, J=8.0, 1.1 Hz, 1H), 7.22 (d, J=2.6 Hz, 1H), 7.19-7.11 (m, 2H), 7.10-7.02 (m, 1H), 6.59 (s, 1H), 5.96 (s, 1H), 3.96 (s, 3H).

Scheme 2.

General Formula 2

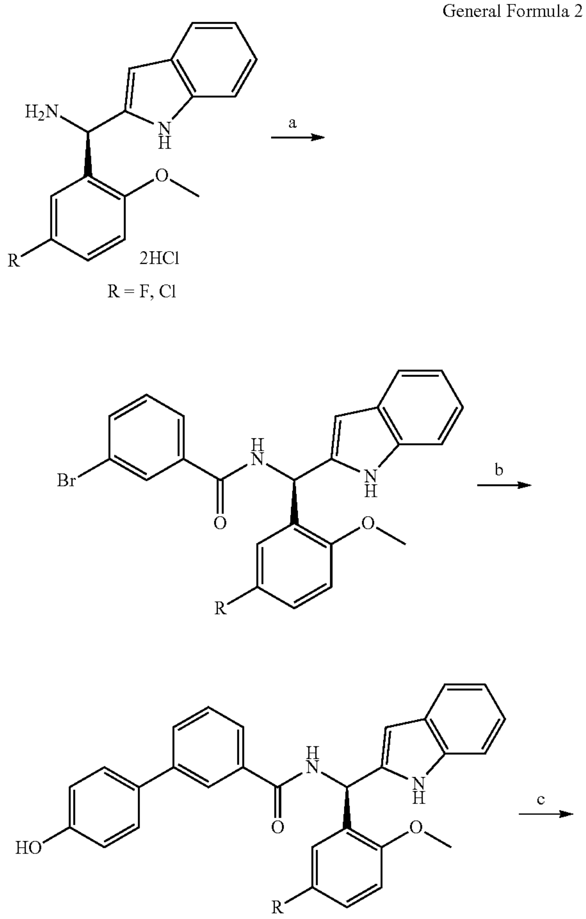

-continued

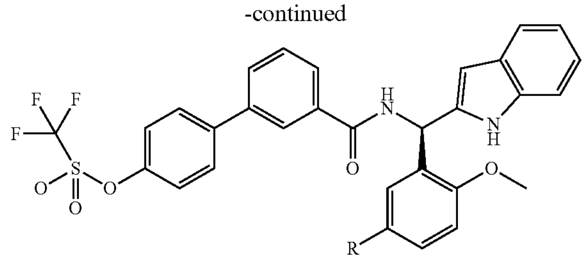

Reagents and conditions:
(a) 3-bromobenzoic acid, 1-ethyl-3-(3-dimethylaminopropyl)carbodiimide, hydroxybenzotriazole, triethylamine, $CH_2Cl_2$, rt, 하룻밤 (overnight);
(b) 4-(4,4,5,5-tetramethyl-1,3,2-dioxaborolene-2-yl)phenol, $Pd(OAc)_2$, Sphos, $Na_2CO_3$, dioxane/$H_2O$, 100° C., overnight;
(c) 1,1,1-trifluoro-N-phenyl-N-((trifluoromethyl)sulfonyl) methanesulfonamide, triethylamine, 4-dimethylaminopyridine, $CH_2Cl_2$, rt, 3 h.

Preparative Example 9: Preparation of (R)-3-bromo-N-((5-fluoro-2-methoxyphenyl)(1H-indole-2-yl)methyl)benzamide

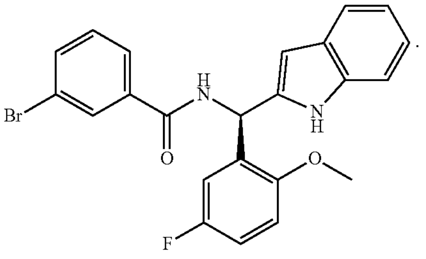 [SMILES: COc1ccc(F)cc1[C@@H](NC(=O)c1cccc(Br)c1)c1cc2ccccc2[nH]1]

Triethylamine (0.11 ml, 0.41 mmol) was added to a solution of (R)-(5-fluoro-2-methoxyphenyl)(1H-indole-2-yl)methaneamine (100 mg, 0.37 mmol), 3-bromobenzoic acid (74.3 mg, 0.37 mmol), 1-ethyl-3-(3-dimethylaminopropyl)carbodiimide (79 mg, 0.41 mmol), and hydroxybenzotriazole (55.4 mg, 0.41 mmol) dissolved in $CH_2Cl_2$ at room temperature. The mixture was stirred overnight. The residue was extracted with water and sodium bicarbonate, and washed with brine. The organic layer was dried over magnesium sulfate, filtered and concentrated. The crude compound was purified by MPLC to give (R)-3-bromo-N-((5-fluoro-2-methoxyphenyl)(1H-indole-2-yl)methyl) benzamide [Preparative Example 9] (134 mg, 80%) as a yellow solid.

$^1$H NMR (300 MHz, chloroform-d) δ 8.86 (s, 1H), 7.95 (t, J=1.8 Hz, 1H), 7.76-7.61 (m, 3H), 7.48 (dq, J=7.1, 0.8 Hz, 1H), 7.35-7.28 (m, 2H), 7.18-7.10 (m, 2H), 7.09-7.02 (m, 2H), 6.97 (dd, J=9.0, 4.4 Hz, 1H), 6.69-6.65 (m, 1H), 6.04 (dt, J=2.0, 1.0 Hz, 1H), 3.87 (s, 3H).

Preparative Example 10: Preparation of (R)-3-bromo-N-((5-chloro-2-methoxyphenyl)(1H-indole-2-yl)methyl)benzamide

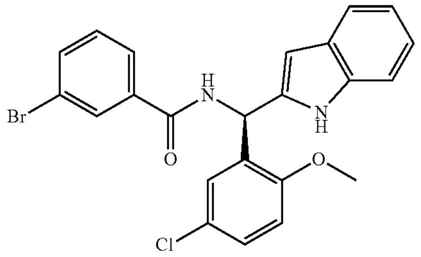 [SMILES: COc1ccc(Cl)cc1[C@@H](NC(=O)c1cccc(Br)c1)c1cc2ccccc2[nH]1]

(R)-3-bromo-N-((5-chloro-2-methoxyphenyl)(1H-indole-2-yl)methyl)benzamide [Preparative Example 10] (75%) was prepared by a method similar to the method described in [Preparative Example 9].

$^1$H NMR (300 MHz, chloroform-d) δ 7.95 (t, J=1.9 Hz, 1H), 7.74-7.67 (m, 2H), 7.67-7.61 (m, 1H), 7.48 (dd, J=7.8, 1.1 Hz, 1H), 7.40 (d, J=2.6 Hz, 1H), 7.36-7.29 (m, 3H), 7.14 (ddd, J=8.2, 7.1, 1.3 Hz, 1H), 7.05 (ddd, J=8.1, 7.1, 1.1 Hz, 1H), 6.95 (d, J=8.8 Hz, 1H), 6.69 (d, J=8.3 Hz, 1H), 6.06 (dt, J=2.0, 0.9 Hz, 1H), 3.87 (d, J=1.3 Hz, 3H).

Preparative Example 11: Preparation of (R)—N-((5-fluoro-2-methoxyphenyl)(1H-indole-2-yl)methyl)-4'-hydroxy-[1,1'-biphenyl]-3-carboxamide

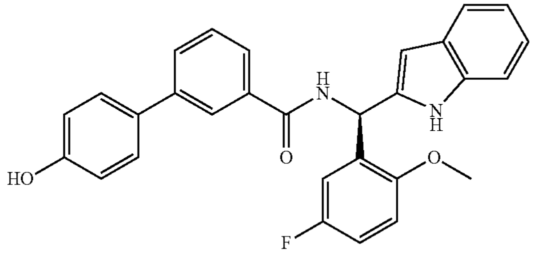 [SMILES: COc1ccc(Cl)cc1[C@@H](NC(=O)c1cccc(-c2ccc(O)cc2)c1)c1cc2ccccc2[nH]1]

4-(4,4,5,5-tetramethyl-1,3,2-dioxaborolene-2-yl)phenol (1281 mg, 3.3 mmol), (R)-3-bromo-N-((5-fluoro-2-methoxyphenyl)(1H-indole-2-yl)methyl)benzamide [Preparative Example 9] (500 mg, 0.05 mmol), $Pd(OAc)_2$ (12.6 mg, 0.055 mmol), Sphos (45.15 mg, 0.11 mmol), and sodium carbonate (349.8 mg, 3.3 mmol) were degassed in 1,4-dioxane/$H_2O$ (4.4/1.1 mL) for 10 minutes. The stirred suspension was heated at 100° C. overnight, diluted with ethyl acetate and washed with water and brine. The organic layer was dried over magnesium sulfate and then concentrated. The residue was purified by MPLC to give (R)—N-((5-fluoro-2-methoxyphenyl)(1H-indole-2-yl)methyl)-4'-hydroxy-[1,1'-biphenyl]-3-carboxamide [Preparative Example 11] (500 mg, 97%) as a yellow solid.

$^1$H NMR (300 MHz, chloroform-d) δ 8.86 (s, 1H), 8.02 (t, J=1.9 Hz, 1H), 7.82 (d, J=8.3 Hz, 1H), 7.71-7.64 (m, 2H), 7.47 (ddd, J=9.7, 8.3, 1.8 Hz, 4H), 7.40 (d, J=8.6 Hz, 1H), 7.33 (dd, J=8.0, 1.0 Hz, 1H), 7.20-7.10 (m, 2H), 7.09-7.02 (m, 2H), 6.99 (d, J=4.5 Hz, 1H), 6.92 (d, J=8.6 Hz, 2H), 6.88 (d, J=8.6 Hz, 1H), 6.72 (d, J=8.3 Hz, 1H), 6.06 (s, 1H), 3.87 (s, 3H).

Preparative Example 12: Preparation of (R)—N-((5-chloro-2-methoxyphenyl)(1H-indole-2-yl)methyl)-4'-hydroxy-[1,1'-biphenyl]-3-carboxamide

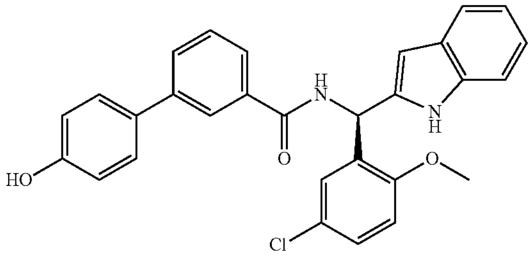

(R)—N-((5-chloro-2-methoxyphenyl)(1H-indole-2-yl)methyl)-4'-hydroxy-[1,1'-biphenyl]-3-carboxamide [Preparative Example 12] (90%) was prepared by a method similar to the method described in [Preparative Example 11].

$^1$H NMR (300 MHz, methanol-$d_4$) δ 8.10 (t, J=1.8 Hz, 1H), 7.78 (ddt, J=13.7, 7.9, 1.3 Hz, 2H), 7.53 (dd, J=8.0, 5.5 Hz, 3H), 7.49-7.43 (m, 1H), 7.39-7.30 (m, 3H), 7.11-7.03 (m, 2H), 6.98 (ddd, J=8.0, 7.1, 1.1 Hz, 1H), 6.92-6.86 (m, 3H), 6.12 (t, J=1.0 Hz, 1H), 3.86 (s, 3H).

Preparative Example 13: Preparation of (R)-3'-(((5-fluoro-2-methoxyphenyl)(1H-indole-2-yl)methyl)carbamoyl)-[1,1'-biphenyl]-4-yl-trifluoromethanesulfonate

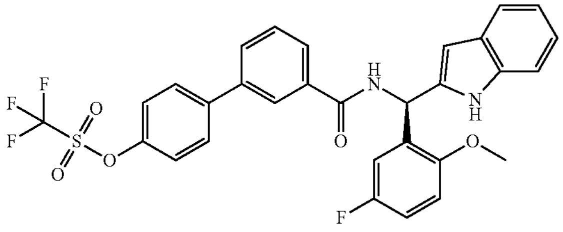 [SMILES: COc1ccc(F)cc1[C@@H](NC(=O)c1cccc(-c2ccc(OS(=O)(=O)C(F)(F)F)cc2)c1)c1cc2ccccc2[nH]1]

Triethylamine (0.47 ml, 3.36 mmol) was added to a solution of (R)—N-((5-fluoro-2-methoxyphenyl)(1H-indole-2-yl)methyl)-4'-hydroxy-[1,1'-biphenyl]-3-carboxamide [Preparative Example 11] (1000 mg, 2.14 mmol), 1,1,1-trifluoro-N-phenyl-N-((trifluoromethyl)sulfonyl)methanesulfonamide (1062 mg, 2.57 mmol), and 4-dimethylaminopyridine (8.8 mg, 0.072 mmol) dissolved in anhydrous $CH_2Cl_2$ at room temperature. The mixture was stirred for 3 hours. The residue was extracted with water and sodium bicarbonate, and washed with brine. The organic layer was dried over magnesium sulfate, filtered and concentrated. The crude compound was purified by MPLC to give (R)-3'-(((5-fluoro-2-methoxyphenyl)(1H-indole-2-yl)methyl)carbamoyl)-[1,1'-biphenyl]-4-yl-trifluoromethanesulfonate [Preparative Example 13] (1030 mg, 80%) as a yellow solid.

$^1$H NMR (300 MHz, chloroform-d) δ 8.07 (t, J=1.7 Hz, 1H), 7.85-7.75 (m, 2H), 7.72 (ddd, J=7.8, 1.9, 1.1 Hz, 1H), 7.69-7.64 (m, 2H), 7.58-7.48 (m, 2H), 7.41-7.33 (m, 3H), 7.22-7.14 (m, 2H), 7.13-7.05 (m, 2H), 7.01 (dd, J=9.0, 4.4 Hz, 1H), 6.74 (d, J=8.2 Hz, 1H), 6.08 (s, 1H), 3.90 (s, 3H).

Preparative Example 14: Preparation of (R)-3'-(((5-chloro-2-methoxyphenyl)(1H-indole-2-yl)methyl)carbamoyl)-[1,1'-biphenyl]-4-yl-trifluoromethanesulfonate

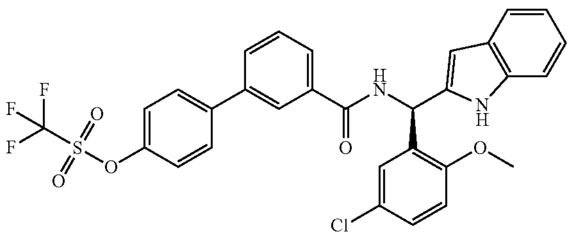 [SMILES: COc1ccc(Cl)cc1[C@@H](NC(=O)c1cccc(-c2ccc(OS(=O)(=O)C(F)(F)F)cc2)c1)c1cc2ccccc2[nH]1]

(R)-3'-(((5-chloro-2-methoxyphenyl)(1H-indole-2-yl)methyl)carbamoyl)-[1,1'-biphenyl]-4-yl-trifluoromethanesulfonate [Preparative Example 14] (85%) was prepared by a method similar to the method described in [Preparative Example 13]: LC-MS (M+H$^+$) calcd for $C_{30}H_{22}ClF_3N_2O_5S$ 614.1, found 615.3.

Scheme 3.

General Formula 3

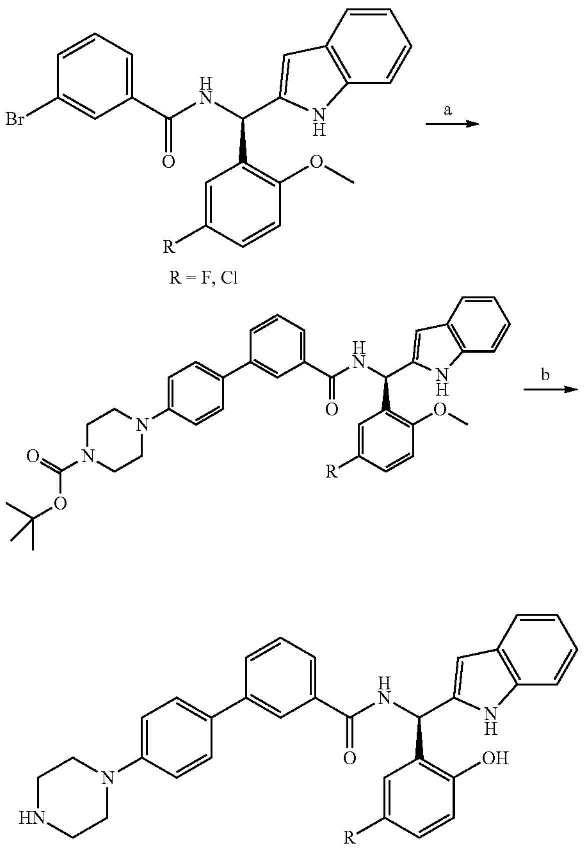

Reagents and conditions:
(a) tert-butyl 4-(4-(4,4,5,5-tetramethyl-1,3,2-dioxaborolene-2-yl)piperazine-1-carboxylate, $Pd(OAc)_2$, Sphos, $Na_2CO_3$, dioxane/$H_2O$, 100° C., overnight;
(b) 1 M $BBr_3$ dissolved in $CH_2Cl_2$, -78° C. to rt, overnight.

Preparative Example 15: Preparation of tert-butyl (R)-4-(3'-(((5-fluoro-2-methoxyphenyl)(1H-indole-2-yl)methyl)carbamoyl)-[1,1'-biphenyl]-4-yl)piperazine-1-carboxylate

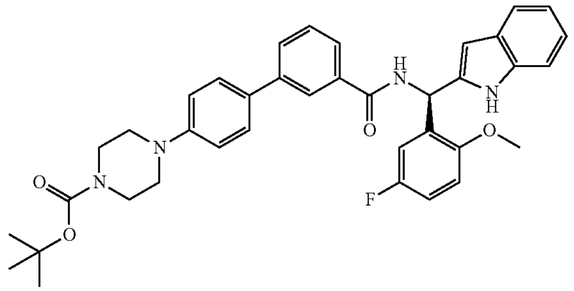 [SMILES: COc1ccc(F)cc1[C@@H](NC(=O)c1cccc(-c2ccc(N3CCN(C(=O)OC(C)(C)C)CC3)cc2)c1)c1cc2ccccc2[nH]1]

Tert-butyl 4-(4-(4,4,5,5-tetramethyl-1,3,2-dioxaborolene-2-yl)phenyl)piperazine-1-carboxylate (77 mg, 0.198 mmol), (R)-3-bromo-N-((5-fluoro-2-methoxyphenyl)(1H-indole-2-yl)methyl)benzamide [Preparative Example 9](30 mg, 0.066 mmol), $Pd(OAc)_2$ (0.7 mg, 0.003 mmol), Sphos (2.5 mg, 0.006 mmol), and sodium carbonate (21 mg, 0.198 mmol) were degassed in 1,4-dioxane/$H_2O$ (0.264/0.066 mL) for 10 minutes. The stirred suspension was heated at 100° C. overnight, diluted with ethyl acetate and washed with water and brine. The organic layer was dried over magnesium sulfate and then concentrated. The residue was purified by MPLC to give tert-butyl (R)-4-(3'-(((5-fluoro-2-methoxyphenyl)(1H-indole-2-yl)methyl)carbamoyl)-[1,1'-biphenyl]-4-yl)piperazine-1-carboxylate [Preparative Example 15] (29.2 mg, 70%) as a yellow solid.

$^1H$ NMR (400 MHz, methanol-$d_4$) δ 8.12 (s, 1H), 7.92 (t, J=2.1 Hz, 1H), 7.79 (t, J=10.1 Hz, 2H), 7.61 (dd, J=8.7, 2.5 Hz, 2H), 7.55-7.43 (m, 2H), 7.37-7.32 (m, 1H), 7.16 (d, J=9.4 Hz, 1H), 7.11-7.03 (m, 5H), 7.01-6.95 (m, 1H), 6.93 (d, J=2.7 Hz, 1H), 6.14-6.09 (m, 1H), 3.85 (t, J=2.1 Hz, 3H), 3.59 (d, J=5.9 Hz, 4H), 3.19 (dt, J=6.9, 3.7 Hz, 4H), 1.55-1.47 (m, 9H).

Preparative Example 16: Preparation of tert-butyl (R)-4-(3'-(((5-chloro-2-methoxyphenyl)(1H-indole-2-yl)methyl)carbamoyl)-[1,1'-biphenyl]-4-yl)piperazine-1-carboxylate

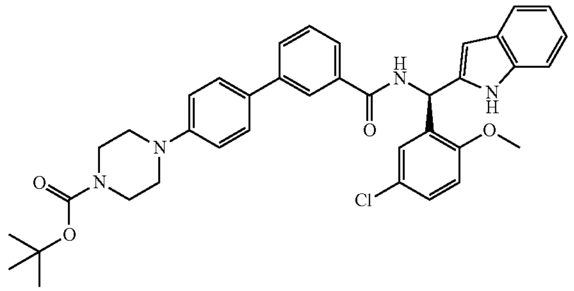 [SMILES: COc1ccc(Cl)cc1[C@@H](NC(=O)c1cccc(-c2ccc(N3CCN(C(=O)OC(C)(C)C)CC3)cc2)c1)c1cc2ccccc2[nH]1]

Tert-butyl (R)-4-(3'-(((5-chloro-2-methoxyphenyl)(1H-indole-2-yl)methyl)carbamoyl)-[1,1'-biphenyl]-4-yl)piperazine-1-carboxylate [Preparative Example 16] (75%) was prepared by a method similar to the method described in [Preparative Example 15].

Example 1: Preparation of (R)—N-((5-fluoro-2-hydroxyphenyl)(1H-indole-2-yl)methyl)-4'-(piperazine-1-yl)-[1,1'-biphenyl]-3-carboxamide

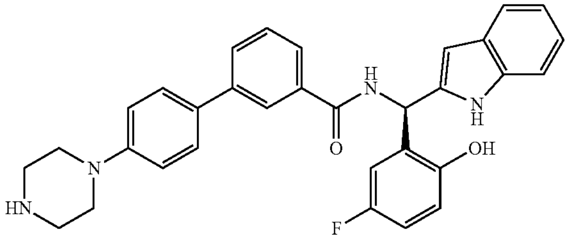 [SMILES: O=C(N[C@@H](c1cc2ccccc2[nH]1)c1cc(F)ccc1O)c1cccc(-c2ccc(N3CCNCC3)cc2)c1]

1 M boron tribromide dissolved in methylene chloride (0.28 ml) was slowly added to tert-butyl (R)-4-(3'-(((5-fluoro-2-methoxyphenyl)(1H-indole-2-yl)methyl)carbamoyl)-[1,1'-biphenyl]-4-yl)piperazine-1-carboxylate [Preparative Example 15] (29.2 mg, 0.046 mmol) at −78° C. The reaction mixture was stirred at room temperature overnight, and sodium bicarbonate was added at 0° C. to terminate the reaction. Tetrahydrofuran was added thereto along with brine. The collected organic layer was dried over $MgSO_4$, filtered and concentrated. The residue was purified by reverse-phase semi-prep HPLC to give (R)—N-((5-fluoro-2-hydroxyphenyl)(1H-indole-2-yl)methyl)-4'-(piperazine-1-yl)-[1,1'-biphenyl]-3-carboxamide [Example 1] (6.3 mg, 26%) as a white solid.

$^1H$ NMR (300 MHz, methanol-$d_4$) δ 8.14 (t, J=1.8 Hz, 1H), 7.87-7.77 (m, 2H), 7.66 (d, J=8.8 Hz, 2H), 7.54 (t, J=7.8 Hz, 1H), 7.46 (dt, J=7.8, 1.0 Hz, 1H), 7.34 (dd, J=8.1, 1.0 Hz, 1H), 7.17-7.11 (m, 2H), 7.10-7.03 (m, 2H), 7.02-6.82 (m, 4H), 6.20 (t, J=0.9 Hz, 1H), 3.48 (dd, J=7.2, 3.7 Hz, 4H), 3.41 (d, J=6.2 Hz, 4H).

Scheme 4.

General Formula 4

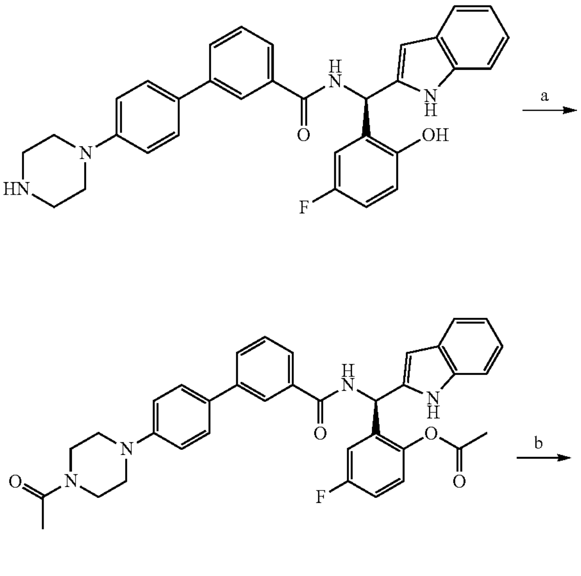

-continued

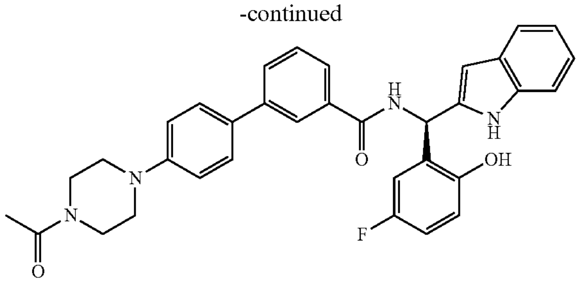

Reagents and conditions:
(a) acetic anhydride, $Et_3N$, $CH_2Cl_2$, 0° C. to rt, 4 h;
(b) $K_2CO_3$, MeOH, reflux, overnight.

Preparative Example 17: Preparation of (R)-2-((4'-(4-acetylpiperazine-1-yl)-[1,1'-biphenyl]-3-carboxamido)(1H-indole-2-yl)methyl)-4-fluorophenyl acetate

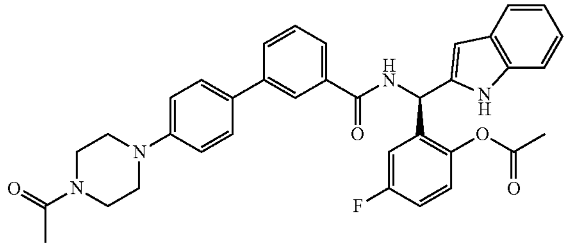 [SMILES: CC(=O)Oc1ccc(F)cc1[C@@H](NC(=O)c1cccc(-c2ccc(N3CCN(C(C)=O)CC3)cc2)c1)c1cc2ccccc2[nH]1]

Acetic anhydride (0.02 ml, 0.18 mmol) was added to a solution of (R)—N-((5-fluoro-2-hydroxyphenyl)(1H-indole-2-yl)methyl)-4'-(piperazine-1-yl)-[1,1'-biphenyl]-3-carboxamide [Example 1] (50 mg, 0.09 mmol) and triethylamine (0.03 ml, 0.18 mmol) at 0° C. The mixture was stirred for 4 hours. The residue was extracted with water and sodium bicarbonate, and washed with brine. The organic layer was dried over magnesium sulfate, filtered, and concentrated to give (R)-2-((4'-(4-acetylpiperazine-1-yl)-[1,1'-biphenyl]-3-carboxamido)(1H-indole-2-yl)methyl)-4-fluorophenyl acetate [Preparative Example 17] (70 mg, yellow solid), which was used in the next step without further purification: LC-MS ($M+H^+$) calcd for C36H33FN4O4 562.24, found 563.5.

Example 2: Preparation of (R)-4'-(4-acetylpiperazine-1-yl)-N-((5-fluoro-2-hydroxyphenyl)(1H-indole-2-yl)methyl)-[1,1'-biphenyl]-3-carboxamide

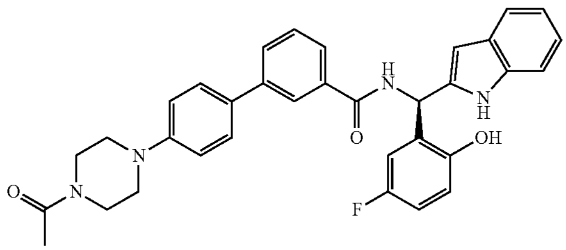 [SMILES: CC(=O)N1CCN(c2ccc(-c3cccc(C(=O)N[C@@H](c4cc5ccccc5[nH]4)c4cc(F)ccc4O)c3)cc2)CC1]

Potassium carbonate (50 mg, 0.36 mmol) was added to a solution of (R)-2-((4'-(4-acetylpiperazine-1-yl)-[1,1'-biphenyl]-3-carboxamido)(1H-indole-2-yl)methyl)-4-fluorophenyl acetate [Preparative Example 17] (51 mg, 0.09 mmol) dissolved in methanol (10 ml) at room temperature. The mixture was stirred at reflux overnight. The residue was concentrated, diluted with methylene chloride and washed with water and brine. The organic layer was concentrated and purified by reverse-phase semi-prep HPLC to give (R)-4'-(4-acetylpiperazine-1-yl)-N-((5-fluoro-2-hydroxyphenyl)(1H-indole-2-yl)methyl)-[1,1'-biphenyl]-3-carboxamide [Example 2] (12 mg, 24%) as a brown solid.

$^1H$ NMR (500 MHz, methanol-$d_4$) δ 8.13 (d, J=2.0 Hz, 1H), 7.79 (dd, J=18.8, 7.8 Hz, 2H), 7.64-7.59 (m, 2H), 7.55-7.50 (m, 1H), 7.46 (d, J=7.9 Hz, 1H), 7.34 (d, J=8.1 Hz, 1H), 7.10-7.05 (m, 4H), 6.98 (t, J=7.5 Hz, 1H), 6.95-6.84 (m, 3H), 6.20 (s, 1H), 3.72 (dt, J=26.4, 4.9 Hz, 4H), 3.22 (ddd, J=26.9, 7.6, 3.3 Hz, 4H), 2.15 (d, J=1.5 Hz, 3H).

Scheme 5.

General Formula 5

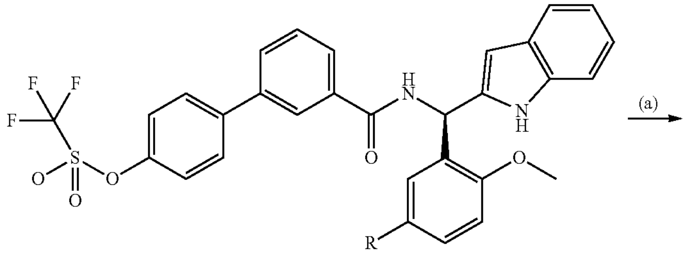

(a)

R4 = F, Cl

-continued

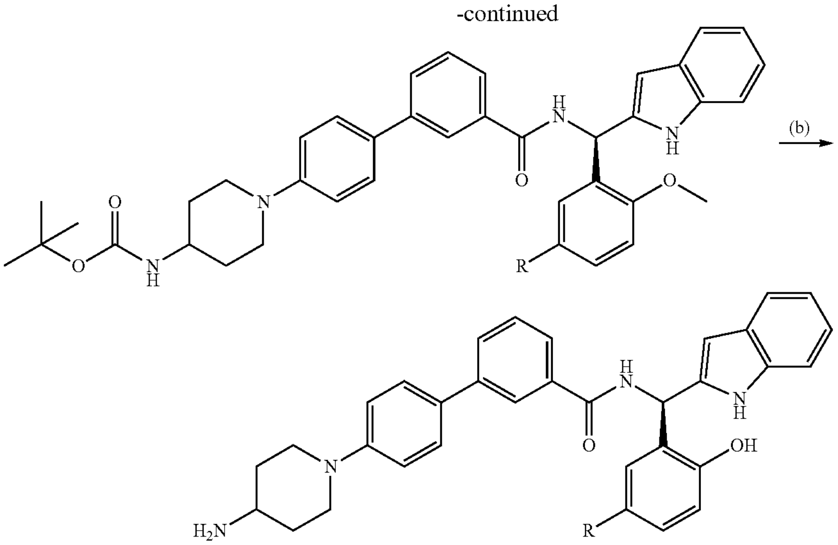

Reagents and conditions:
(a) tert-butyl piperidine-4-ylcarbamate, Ruphos Pd G1, $Cs_2CO_3$, dioxane, 110° C., overnight;
(b) 1 M $BBr_3$ dissolved in $CH_2Cl_2$, 0° C. to rt, 30 minutes.

Preparative Example 18: Preparation of tert-butyl (R)-(1-(3'-(((5-fluoro-2-methoxyphenyl)(1H-indole-2-yl)methyl)carbamoyl)-[1,1'-biphenyl]-4-yl)piperidine-4-yl)carbamate

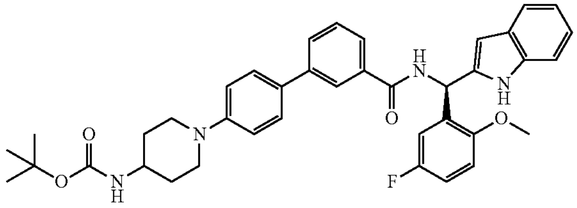 [SMILES: COc1ccc(F)cc1[C@@H](NC(=O)c1cccc(-c2ccc(N3CCC(NC(=O)OC(C)(C)C)CC3)cc2)c1)c1cc2ccccc2[nH]1]

Tert-butyl piperidine-4-ylcarbamate (50.1 mg, 0.25 mmol), (R)-3'-(((5-fluoro-2-methoxyphenyl)(1H-indole-2-yl)methyl)carbamoyl)-[1,1'-biphenyl]-4-yl-trifluoromethanesulfonate [Preparative Example 13] (50 mg, 0.083 mmol), Ruphos Pd G1 (1.01 mg, 0.001 mmol), and cesium carbonate (81.4 mg, 0.25 mmol) were degassed in anhydrous 1,4-dioxane (0.4 mL) for 10 minutes. The stirred suspension was heated at 110° C. overnight, diluted with ethyl acetate, and washed with water and brine. The organic layer was dried over magnesium sulfate and concentrated to give tert-butyl (R)-(1-(3'-(((5-fluoro-2-methoxyphenyl)(1H-indole-2-yl)methyl)carbamoyl)-[1,1'-biphenyl]-4-yl)piperidine-4-yl)carbamate [Preparative Example 18] (yellow solid), which was used in the next step without further purification: LC-MS ($M+H^+$) calcd for $C_{39}H_{41}FN_4O_4$ 648.31, found 649.2.

Preparative Example 19: Preparation of tert-butyl (R)-(1-(3'-(((5-chloro-2-methoxyphenyl)(1H-indole-2-yl)methyl)carbamoyl)-[1,1'-biphenyl]-4-yl)piperidine-4-yl)carbamate

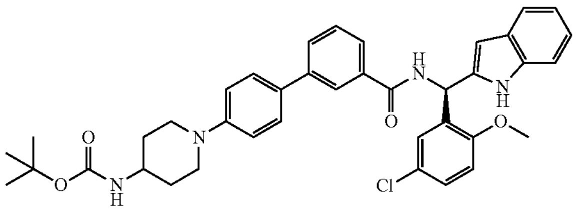 [SMILES: COc1ccc(Cl)cc1[C@@H](NC(=O)c1cccc(-c2ccc(N3CCC(NC(=O)OC(C)(C)C)CC3)cc2)c1)c1cc2ccccc2[nH]1]

Tert-butyl (R)-(1-(3'-(((5-chloro-2-methoxyphenyl)(1H-indole-2-yl)methyl)carbamoyl)-[1,1'-biphenyl]-4-yl)piperidine-4-yl)carbamate [Preparative Example 19] was prepared by a method similar to the method described in [Preparative Example 18]: LC-MS ($M+H^+$) calcd for $C_{39}H_{41}ClN_4O_4$ 664.28, found 665.3.

Example 3: Preparation of (R)-4'-(4-aminopiperidine-1-yl)-N-((5-fluoro-2-hydroxyphenyl)(1H-indole-2-yl)methyl)-[1,1'-biphenyl]-3-carboxamide

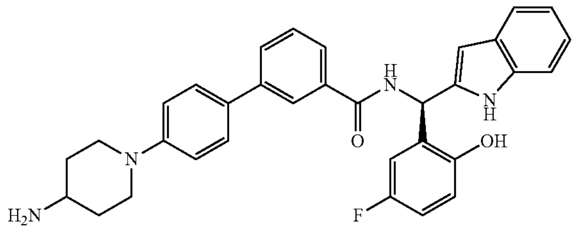 [SMILES: NC1CCN(c2ccc(-c3cccc(C(=O)N[C@@H](c4cc5ccccc5[nH]4)c4cc(F)ccc4O)c3)cc2)CC1]

(R)-4'-(4-aminopiperidine-1-yl)-N-((5-fluoro-2-hydroxyphenyl)(1H-indole-2-yl)methyl)-[1,1'-biphenyl]-3-carboxamide [Example 3] (20%) was prepared by a method similar to the method described in [Example 1].

$^1$H NMR (300 MHz, methanol-$d_4$) δ 9.23 (d, J=8.3 Hz, 1H), 8.13 (t, J=1.7 Hz, 1H), 7.85-7.74 (m, 2H), 7.63 (d, J=8.8 Hz, 2H), 7.57-7.44 (m, 2H), 7.38-7.32 (m, 1H), 7.13 (d, J=8.8 Hz, 2H), 7.10-7.04 (m, 2H), 7.02-6.82 (m, 4H), 6.21 (d, J=1.0 Hz, 1H), 3.88 (d, J=13.0 Hz, 2H), 2.93 (td, J=12.6, 2.5 Hz, 2H), 2.16-2.07 (m, 2H), 1.80 (qd, J=12.2, 4.0 Hz, 2H).

Example 4: Preparation of (R)-4'-(4-aminopiperidine-1-yl)-N-((5-chloro-2-hydroxyphenyl)(1H-indole-2-yl)methyl)-[1,1'-biphenyl]-3-carboxamide

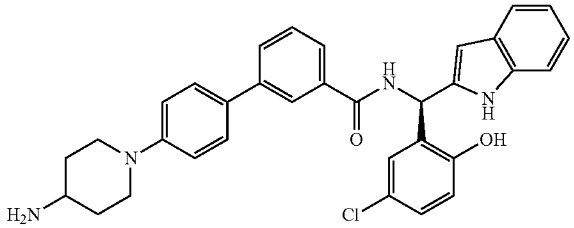 [SMILES: NC1CCN(c2ccc(-c3cccc(C(=O)N[C@@H](c4cc5ccccc5[nH]4)c4cc(Cl)ccc4O)c3)cc2)CC1]

(R)-4'-(4-aminopiperidine-1-yl)-N-((5-chloro-2-hydroxyphenyl)(1H-indole-2-yl)methyl)-[1,1'-biphenyl]-3-carboxamide [Example 4] (35%) was prepared by a method similar to the method described in [Example 1].

$^1$H NMR (500 MHz, methanol-$d_4$) δ 8.17 (d, J=2.0 Hz, 1H), 7.91 (d, J=7.8 Hz, 1H), 7.84 (t, J=7.7 Hz, 3H), 7.58 (d, J=7.7 Hz, 3H), 7.47 (d, J=7.9 Hz, 1H), 7.35 (d, J=8.1 Hz, 1H), 7.29 (t, J=1.8 Hz, 1H), 7.20-7.15 (m, 1H), 7.08 (t, J=7.6 Hz, 1H), 6.98 (t, J=7.5 Hz, 1H), 6.88 (d, J=8.5 Hz, 2H), 3.91 (d, J=12.7 Hz, 2H), 3.56 (dd, J=29.1, 15.4 Hz, 3H), 2.33 (d, J=13.2 Hz, 2H), 2.14 (q, J=12.6 Hz, 2H).

Scheme 6.

General Formula 6

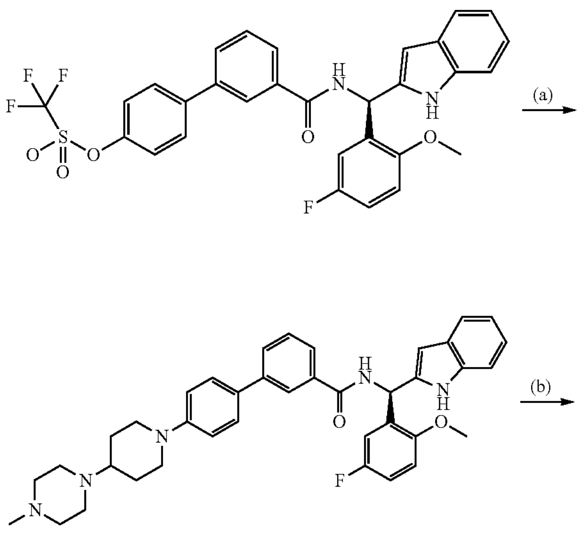

-continued

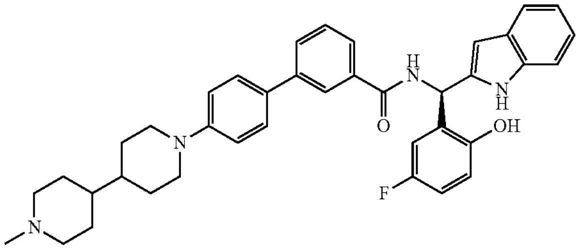

Reagents and conditions:
(a) 1-methyl-4-(piperidine-4-yl)piperazine, Ruphos Pd G1, $Cs_2CO_3$, dioxane, 110° C., overnight;
(b) 1 M $BBr_3$ dissolved in $CH_2Cl_2$, 0° C. to rt, 30 minutes.

Preparative Example 20: Preparation of (R)—N-((5-fluoro-2-methoxyphenyl)(1H-indole-2-yl)methyl)-4'-(4-(4-methylpiperazine-1-yl)piperidine-1-yl)-[1,1'-biphenyl]-3-carboxamide

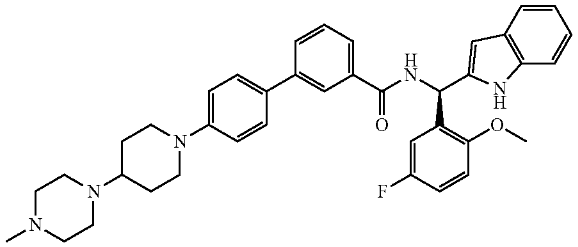

1-Methyl-4-(piperidine-4-yl)piperazine (46 mg, 0.25 mmol), (R)-3'-(((5-fluoro-2-methoxyphenyl)(1H-indole-2-yl)methyl)carbamoyl)-[1,1'-biphenyl]-4-yl-trifluoromethanesulfonate [Preparative Example 13] (50 mg, 0.083 mmol), Ruphos Pd G1 (1.01 mg, 0.001 mmol), and cesium carbonate (81.4 mg, 0.25 mmol) were degassed in anhydrous 1,4-dioxane (0.4 mL) for 10 minutes. The stirred suspension was heated at 110° C. overnight, diluted with ethyl acetate, and washed with water and brine. The organic layer was dried over magnesium sulfate and concentrated. The mixture was purified by MPLC to give (R)—N-((5-fluoro-2-methoxyphenyl)(1H-indole-2-yl)methyl)-4'-(4-(4-methylpiperazine-1-yl)piperidine-1-yl)-[1,1'-biphenyl]-3-carboxamide [Preparative Example 20] (25 mg, 50%) as a yellow solid.

$^1$H NMR (300 MHz, chloroform-d) δ 9.08-8.99 (m, 1H), 8.03 (t, J=1.9 Hz, 1H), 7.83 (dd, J=8.2, 2.3 Hz, 1H), 7.74-7.67 (m, 2H), 7.55-7.44 (m, 4H), 7.35 (dd, J=8.1, 1.0 Hz, 1H), 7.21-7.13 (m, 2H), 7.12-7.04 (m, 2H), 6.98 (td, J=6.4, 3.0 Hz, 3H), 6.74 (dd, J=8.2, 2.9 Hz, 1H), 6.08 (dd, J=2.1, 1.0 Hz, 1H), 3.88 (d, J=1.9 Hz, 3H), 3.82 (d, J=12.7 Hz, 2H), 2.83-2.57 (m, 10H), 2.54-2.46 (m, 1H), 2.43 (s, 3H), 1.96 (d, J=12.2 Hz, 2H), 1.68 (qd, J=12.1, 3.9 Hz, 2H).

Example 5: Preparation of (R)—N-((5-fluoro-2-hydroxyphenyl)(1H-indole-2-yl)methyl)-4'-(4-(4-methylpiperazine-1-yl)piperidine-1-yl)-[1,1'-biphenyl]-3-carboxamide

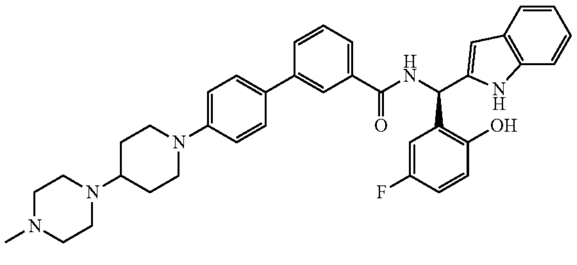

(R)—N-((5-fluoro-2-hydroxyphenyl)(1H-indole-2-yl)methyl)-4'-(4-(4-methylpiperazine-1-yl)piperidine-1-yl)-[1,1'-biphenyl]-3-carboxamide [Example 5] (12%) was prepared by a method similar to the method described in [Example 1].

$^1H$ NMR (300 MHz, methanol-$d_4$) δ 9.26 (d, J=8.4 Hz, 1H), 8.15 (s, 1H), 7.87 (d, J=7.9 Hz, 1H), 7.82 (d, J=8.0 Hz, 1H), 7.74 (d, J=8.7 Hz, 2H), 7.56 (t, J=7.8 Hz, 1H), 7.46 (d, J=7.8 Hz, 1H), 7.39-7.31 (m, 3H), 7.11-7.03 (m, 2H), 7.01-6.95 (m, 1H), 6.95-6.83 (m, 3H), 6.20 (t, J=1.0 Hz, 1H), 3.89 (d, J=12.9 Hz, 3H), 3.25-2.95 (m, 9H), 2.89 (s, 3H), 2.18 (d, J=12.9 Hz, 2H), 1.91 (q, J=11.4, 9.0 Hz, 2H).

Scheme 7.

General Formula 7

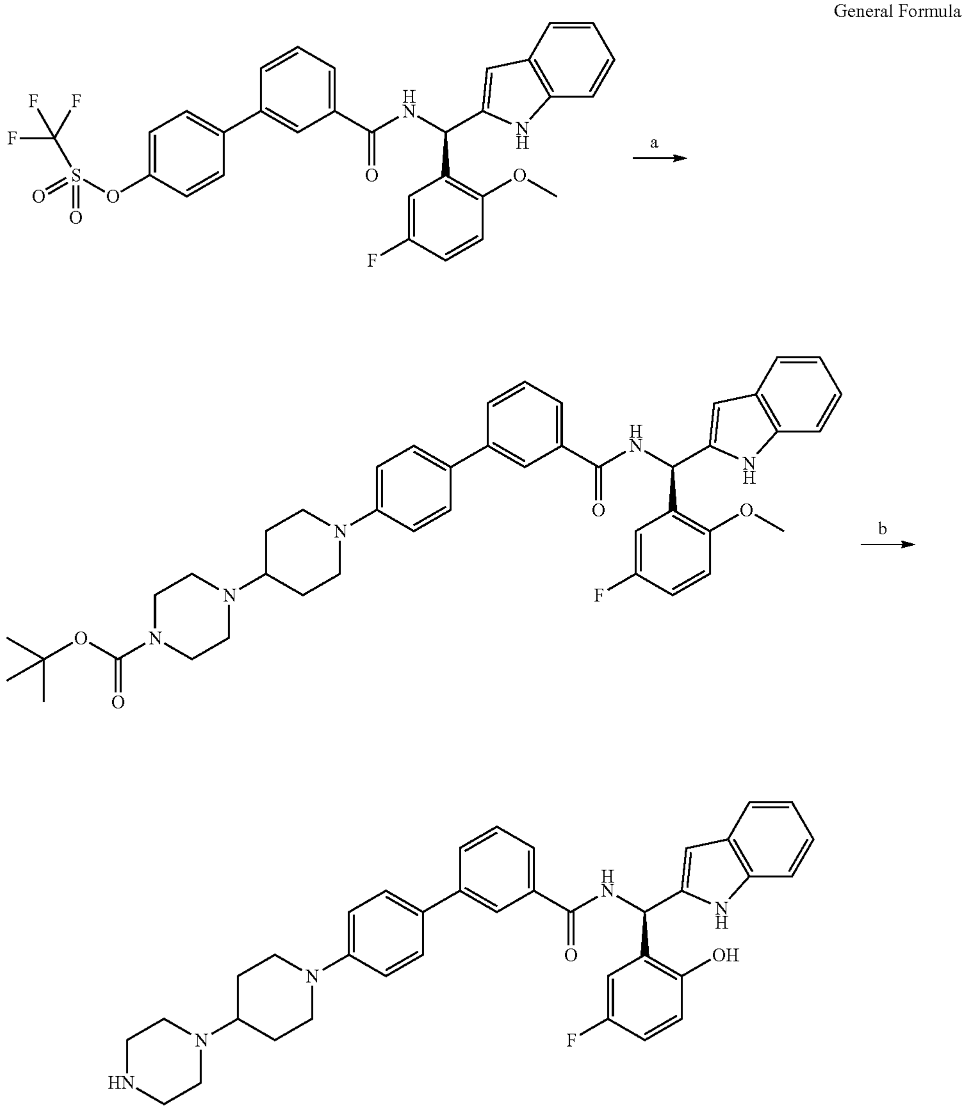

Reagents and conditions: (a) tert-butyl 4-(piperidine-4-yl)piperazine-1-carboxylate, Ruphos Pd G1, $Cs_2CO_3$, dioxane, 110° C., overnight; (b) 1M $BBr_3$ dissolved in $CH_2Cl_2$, 0° C. to rt, 30 minutes.

Preparative Example 21: Preparation of tert-butyl (R)-4-(1-(3'-(((5-fluoro-2-methoxyphenyl)(1H-indole-2-yl)methyl)carbamoyl)-[1,1'-biphenyl]-4-yl)piperidine-4-yl)piperazine-1-carboxylate

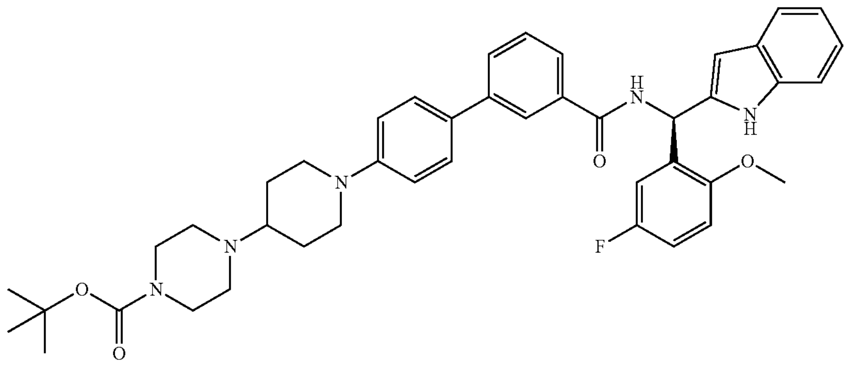

Tert-butyl 4-(piperidine-4-yl)piperazine-1-carboxylate (67 mg, 0.25 mmol), (R)-3'-(((5-fluoro-2-methoxyphenyl)(1H-indole-2-yl)methyl)carbamoyl)-[1,1'-biphenyl]-4-yl-trifluoromethanesulfonate [Preparative Example 13] (50 mg, 0.083 mmol), Ruphos Pd G1 (1.01 mg, 0.001 mmol), and cesium carbonate (81.4 mg, 0.25 mmol) were degassed in anhydrous 1,4-dioxane (0.4 mL) for 10 minutes. The stirred suspension was heated at 110° C. overnight, diluted with ethyl acetate, and washed with water and brine. The organic layer was dried over magnesium sulfate and concentrated. The mixture was purified by MPLC to give tert-butyl (R)-4-(1-(3'-(((5-fluoro-2-methoxyphenyl)(1H-indole-2-yl)methyl)carbamoyl)-[1,1'-biphenyl]-4-yl)piperidine-4-yl)piperazine-1-carboxylate [Preparative Example 21] (19.5 mg, 33%) as a yellow solid.

$^1$H NMR (300 MHz, chloroform-d) δ 9.09-8.90 (m, 1H), 8.01 (t, J=1.9 Hz, 1H), 7.80 (d, J=8.3 Hz, 1H), 7.67 (tt, J=8.1, 1.3 Hz, 2H), 7.53-7.40 (m, 4H), 7.35-7.29 (m, 1H), 7.20-7.12 (m, 2H), 7.12-7.02 (m, 1H), 7.01-6.91 (m, 3H), 6.72 (dd, J=8.2, 4.1 Hz, 1H), 6.07-6.03 (m, 1H), 3.85 (d, J=2.2 Hz, 3H), 3.81 (d, J=13.2 Hz, 2H), 3.46 (t, J=5.0 Hz, 4H), 2.76 (dd, J=13.1, 10.8 Hz, 2H), 2.55 (t, J=5.1 Hz, 4H), 2.46 (t, J=11.4 Hz, 1H), 1.93 (d, J=12.3 Hz, 2H), 1.68 (qd, J=12.0, 3.9 Hz, 2H), 1.47 (s, 9H).

Example 6: Preparation of (R)—N-((5-fluoro-2-hydroxyphenyl)(1H-indole-2-yl)methyl)-4'-(4-(piperazine-1-yl)piperidine-1-yl)-[1,1'-biphenyl]-3-carboxamide

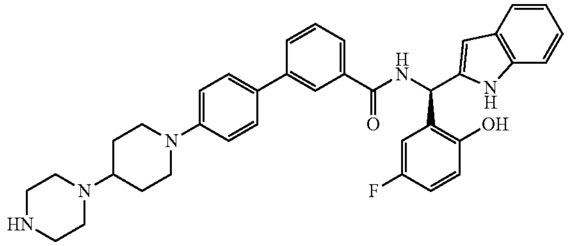 [SMILES: O=C(N[C@@H](c1cc2ccccc2[nH]1)c1cc(F)ccc1O)c1cccc(-c2ccc(N3CCC(N4CCNCC4)CC3)cc2)c1]

(R)—N-((5-fluoro-2-hydroxyphenyl)(1H-indole-2-yl)methyl)-4'-(4-(piperazine-1-yl)piperidine-1-yl)-[1,1'-biphenyl]-3-carboxamide [Example 6] (36.8%) was prepared by a method similar to the method described in [Example 1].

$^1$H NMR (300 MHz, methanol-$d_4$) δ 8.15 (s, 1H), 7.90-7.78 (m, 2H), 7.73 (d, J=8.7 Hz, 2H), 7.56 (t, J=7.8 Hz, 1H), 7.46 (d, J=7.8 Hz, 1H), 7.33 (t, J=7.6 Hz, 3H), 7.11-7.03 (m, 2H), 7.02-6.95 (m, 2H), 6.94-6.83 (m, 2H), 6.20 (d, J=1.0 Hz, 1H), 3.92 (d, J=12.5 Hz, 2H), 3.45 (d, J=5.8 Hz, 5H), 3.17 (d, J=11.8 Hz, 5H), 2.21 (d, J=12.7 Hz, 2H), 1.97 (t, J=12.2 Hz, 3H).

Scheme 8.

General Formula 8

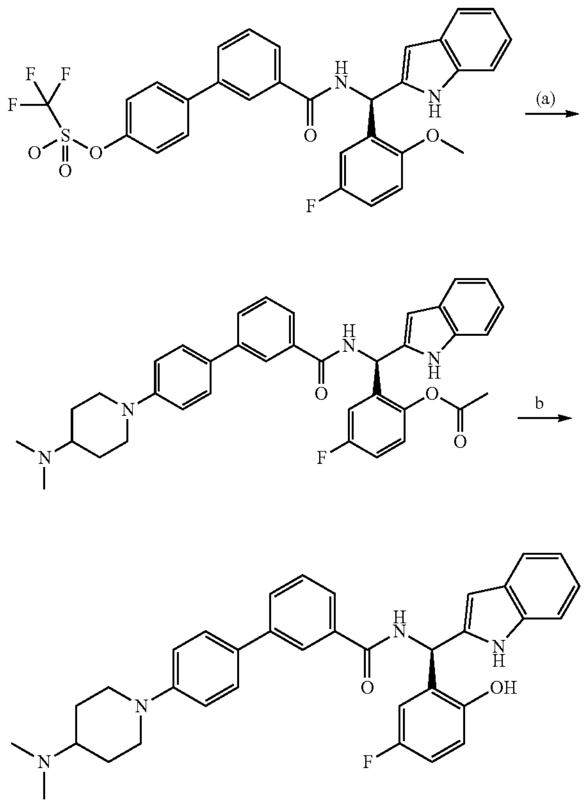

Reagents and conditions:
(a) N,N-dimethylpiperidine-4-amine, Ruphos Pd G1, $Cs_2CO_3$, dioxane, 110° C., overnight;
(b) 1 M $BBr_3$ dissolved in $CH_2Cl_2$, 0° C. to rt, 30 minutes.

Preparative Example 22: Preparation of (R)-4'-(4-(dimethylamino)piperidine-1-yl)-N-((5-fluoro-2-methoxyphenyl)(1H-indole-2-yl)methyl)-[1,1'-biphenyl]-3-carboxamide

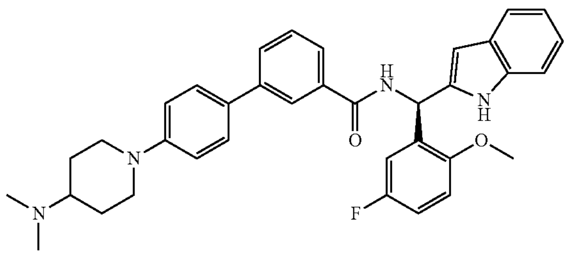 [SMILES: COc1ccc(F)cc1[C@@H](NC(=O)c1cccc(-c2ccc(N3CCC(N(C)C)CC3)cc2)c1)c1cc2ccccc2[nH]1]

N,N-dimethylpiperidine-4-amine (32.05 mg, 0.25 mmol), (R)-3'-(((5-fluoro-2-methoxyphenyl)(1H-indole-2-yl) methyl)carbamoyl)-[1,1'-biphenyl]-4-yl-trifluoromethanesulfonate [Preparative Example 13] (50 mg, 0.083 mmol), Ruphos Pd G1 (1.01 mg, 0.001 mmol), and cesium carbonate (81.4 mg, 0.25 mmol) were degassed in anhydrous 1,4-dioxane (0.4 mL) for 10 minutes. The stirred suspension was heated at 110° C. overnight, diluted with ethyl acetate, and washed with water and brine. The organic layer was dried over magnesium sulfate and concentrated to give (R)-4'-(4-(dimethylamino)piperidine-1-yl)-N-((5-fluoro-2-methoxyphenyl)(1H-indole-2-yl)methyl)-[1,1'-biphenyl]-3-carboxamide [Preparative Example 22] (yellow solid): LC-MS ($M+H^+$) calcd for $C_{36}H_{37}FN_4O_2$ 576.29, found 577.4.

Example 7: Preparation of (R)-4'-(4-(dimethylamino)piperidine-1-yl)-N-((5-fluoro-2-hydroxyphenyl)(1H-indole-2-yl)methyl)-[1,1'-biphenyl]-3-carboxamide

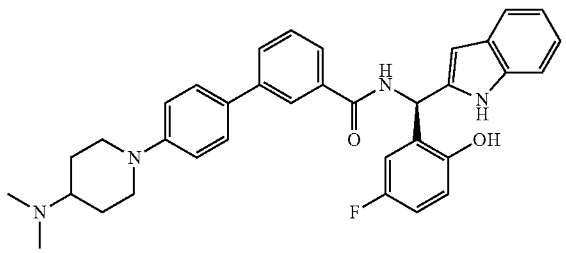 [SMILES: CN(C)C1CCN(c2ccc(-c3cccc(C(=O)N[C@@H](c4cc5ccccc5[nH]4)c4cc(F)ccc4O)c3)cc2)CC1]

(R)-4'-(4-(dimethylamino)piperidine-1-yl)-N-((5-fluoro-2-hydroxyphenyl)(1H-indole-2-yl)methyl)-[1,1'-biphenyl]-3-carboxamide [Example 7] (6.4%) was prepared by a method similar to the method described in [Example 1].

$^1$H NMR (300 MHz, methanol-$d_4$) δ 9.22 (d, J=8.3 Hz, 1H), 8.13 (t, J=1.8 Hz, 1H), 7.80 (ddt, J=12.6, 7.9, 1.2 Hz, 2H), 7.62 (d, J=8.8 Hz, 2H), 7.57-7.49 (m, 1H), 7.46 (dt, J=7.8, 1.2 Hz, 1H), 7.34 (dd, J=8.1, 1.0 Hz, 1H), 7.14-7.04 (m, 4H), 7.01-6.92 (m, 2H), 6.91-6.84 (m, 2H), 6.44 (d, J=8.1 Hz, 1H), 6.21 (d, J=1.0 Hz, 1H), 3.97 (d, J=13.1 Hz, 2H), 2.91 (s, 6H), 2.84 (d, J=12.4 Hz, 1H), 2.18 (d, J=11.8 Hz, 2H), 1.86 (qd, J=12.3, 4.2 Hz, 3H), 1.22 (d, J=10.8 Hz, 2H).

Scheme 9.

General Formula 9

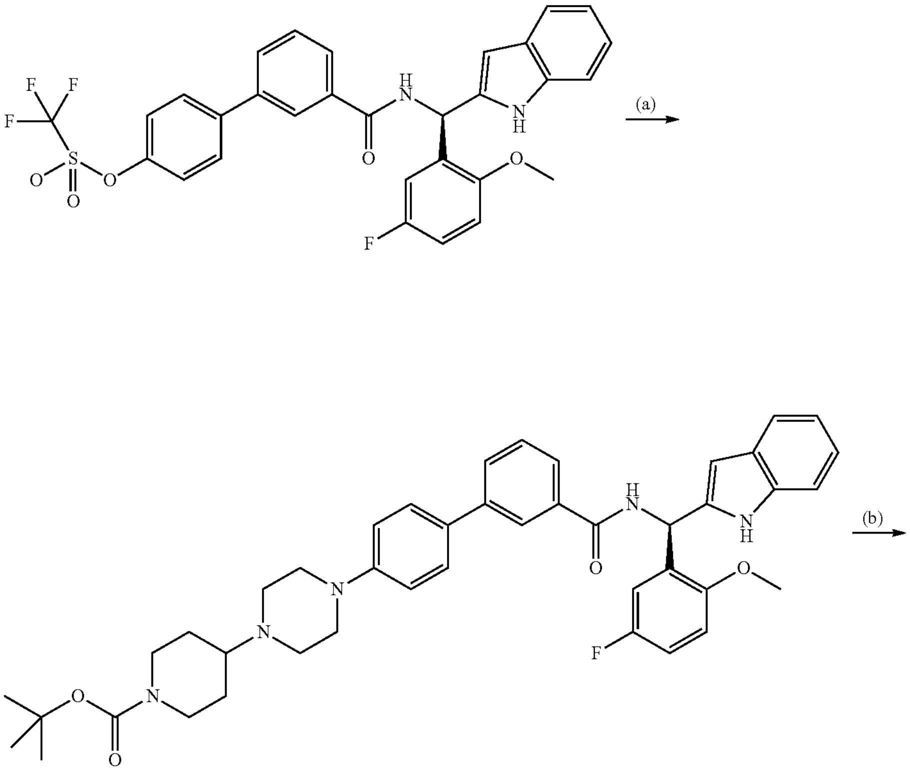

-continued

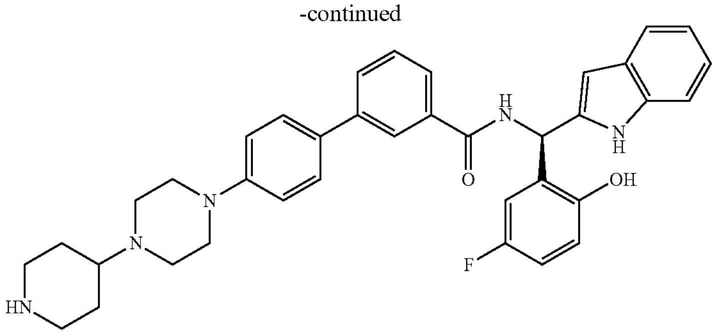

Reagents and conditions:
(a) tert-butyl 4-(piperazine-1-yl)piperidine-1-carboxylate, Ruphos Pd G1, $Cs_2CO_3$, dioxane, 110° C., overnight;
(b) 1 M $BBr_3$ dissolved in $CH_2Cl_2$, 0° C. to rt, 30 minutes.

Preparative Example 23: Preparation of tert-butyl (R)-4-(4-(3'-(((5-fluoro-2-methoxyphenyl)(1H-indole-2-yl)methyl)carbamoyl)-[1,1'-biphenyl]-4-yl) piperazine-1-yl)piperidine-1-carboxylate

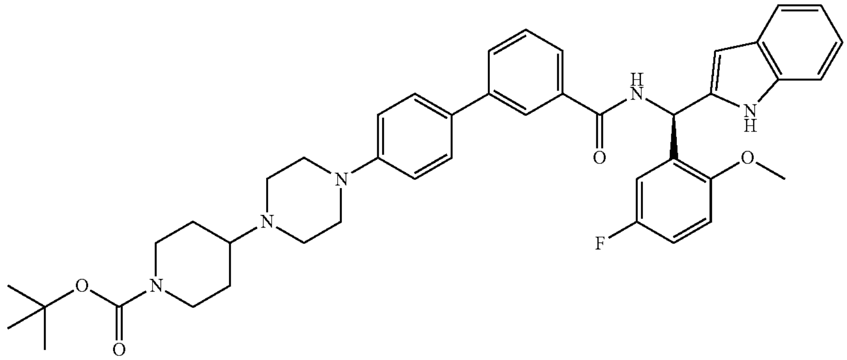 [SMILES: COc1ccc(F)cc1[C@@H](NC(=O)c1cccc(-c2ccc(N3CCN(C4CCN(C(=O)OC(C)(C)C)CC4)CC3)cc2)c1)c1cc2ccccc2[nH]1]

Tert-butyl 4-(piperazine-1-yl)piperidine-1-carboxylate (67 mg, 0.25 mmol), (R)-3'-(((5-fluoro-2-methoxyphenyl) (1H-indole-2-yl)methyl)carbamoyl)-[1,1'-biphenyl]-4-yl-trifluoromethanesulfonate [Preparative Example 13] (50 mg, 0.083 mmol), Ruphos Pd G1 (1.01 mg, 0.001 mmol), and cesium carbonate (81.4 mg, 0.25 mmol) were degassed in anhydrous 1,4-dioxane (0.4 mL) for 10 minutes. The stirred suspension was heated at 110° C. overnight, diluted with ethyl acetate, and washed with water and brine. The organic layer was dried over magnesium sulfate and concentrated to give tert-butyl (R)-4-(4-(3'-(((5-fluoro-2-methoxyphenyl) (1H-indole-2-yl)methyl)carbamoyl)-[1,1'-biphenyl]-4-yl) piperazine-1-yl)piperidine-1-carboxylate [Preparative Example 23] (yellow solid): LC-MS ($M+H^+$) calcd for $C_{43}H_{48}FN_5O_2$ 717.37, found 718.7.

Example 8: Preparation of (R)—N-((5-fluoro-2-hydroxyphenyl)(1H-indole-2-yl)methyl)-4'-(4-(piperidine-4-yl)piperazine-1-yl)-[1,1'-biphenyl]-3-carboxamide

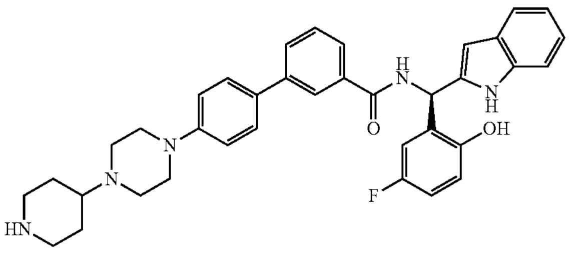

(R)—N-((5-fluoro-2-hydroxyphenyl)(1H-indole-2-yl) methyl)-4'-(4-(piperidine-4-yl)piperazine-1-yl)-[1,1'-biphenyl]-3-carboxamide [Example 8] (12.1%) was prepared by a method similar to the method described in [Example 1].

$^{1}H$ NMR (300 MHz, methanol-$d_4$) δ 8.14 (t, J=1.8 Hz, 1H), 7.84 (d, J=7.7 Hz, 1H), 7.80 (d, J=8.0 Hz, 1H), 7.67 (d, J=8.7 Hz, 2H), 7.54 (t, J=7.8 Hz, 1H), 7.46 (dd, J=7.8, 1.2 Hz, 1H), 7.34 (dd, J=7.9, 1.0 Hz, 1H), 7.13 (d, J=8.8 Hz, 2H), 7.09-7.03 (m, 2H), 7.02-6.95 (m, 1H), 6.94-6.84 (m, 3H), 6.44 (d, J=8.1 Hz, 1H), 6.20 (d, J=1.0 Hz, 1H), 3.71-3.46 (m, 10H), 3.13 (t, J=12.8 Hz, 3H), 2.48 (d, J=13.2 Hz, 2H), 2.12-1.92 (m, 3H).

Scheme 10.

General Formula 10

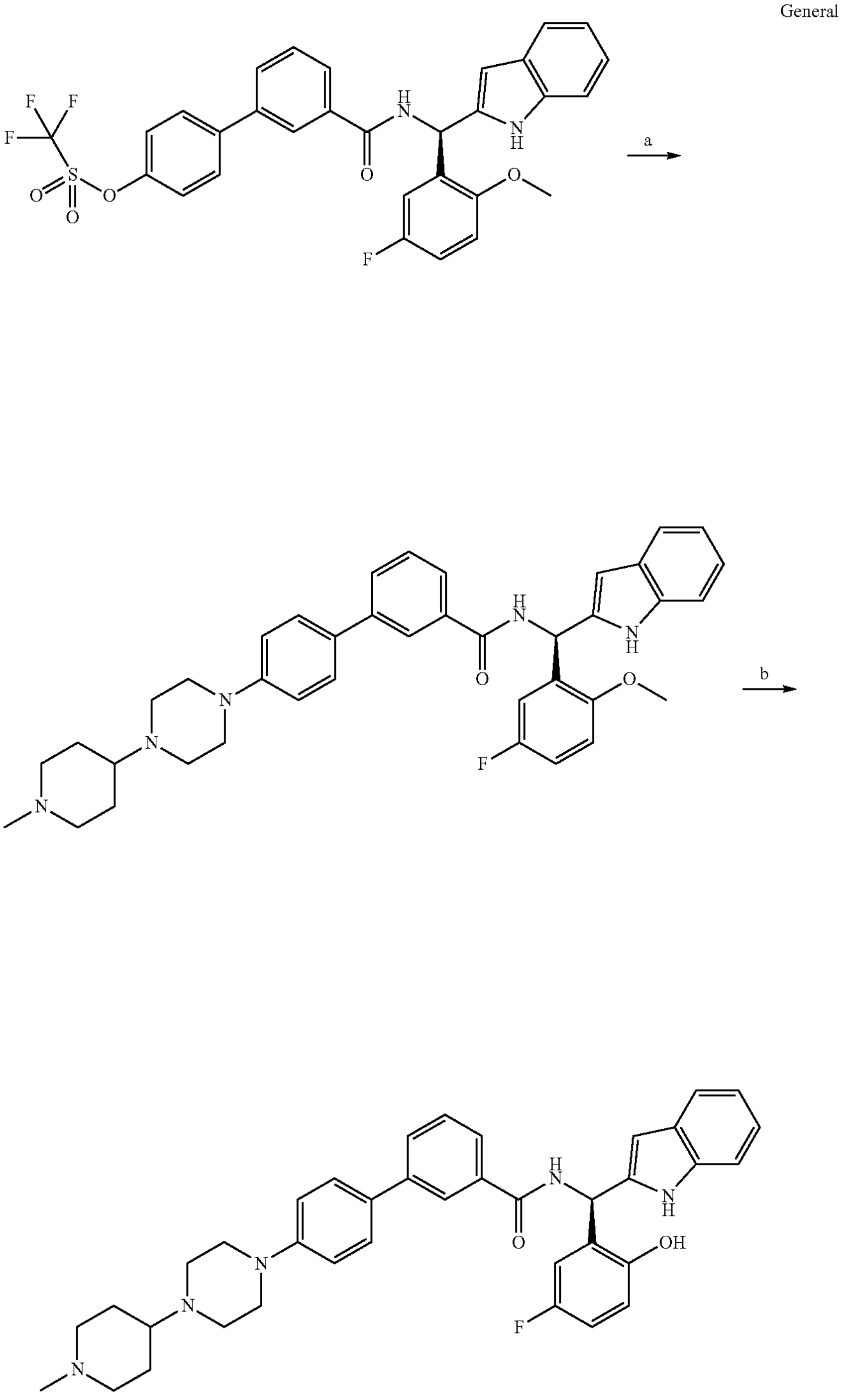

Reagents and conditions: (a) 1-(1-methylpiperidine-4-yl)piperazine, Ruphos Pd G1, $Cs_2CO_3$, dioxane, 110° C., overnight; (b) 1M $BBr_3$ dissolved in $CH_2Cl_2$, 0° C. to rt, 30 minutes.

Preparative Example 24: Preparation of (R)—N-((5-fluoro-2-methoxyphenyl)(1H-indole-2-yl)methyl)-4'-(4-(1-methylpiperidine-4-yl)piperazine-1-yl)-[1,1'-biphenyl]-3-carboxamide

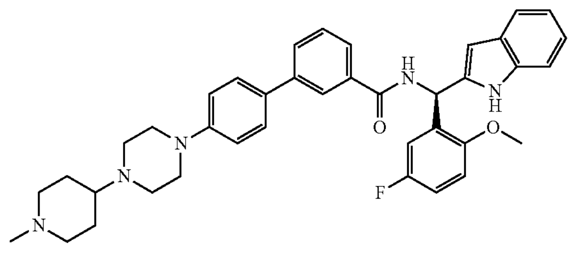 [SMILES: COc1ccc(F)cc1[C@@H](NC(=O)c1cccc(-c2ccc(N3CCN(C4CCN(C)CC4)CC3)cc2)c1)c1cc2ccccc2[nH]1]

1-(1-Methylpiperidine-4-yl)piperazine (46 mg, 0.25 mmol), (R)-3'-(((5-fluoro-2-methoxyphenyl)(1H-indole-2-yl)methyl)carbamoyl)-[1,1'-biphenyl]-4-yl-trifluoromethanesulfonate [Preparative Example 13] (50 mg, 0.083 mmol), Ruphos Pd G1 (1.01 mg, 0.001 mmol), and cesium carbonate (81.4 mg, 0.25 mmol) were degassed in anhydrous 1,4-dioxane (0.4 mL) for 10 minutes. The stirred suspension was heated at 110° C. overnight, diluted with ethyl acetate, and washed with water and brine. The organic layer was dried over magnesium sulfate and concentrated to give (R)—N-((5-fluoro-2-methoxyphenyl)(1H-indole-2-yl)methyl)-4'-(4-(1-methylpiperidine-4-yl)piperazine-1-yl)-[1,1'-biphenyl]-3-carboxamide [Preparative Example 24] as a yellow solid: LC-MS ($M+H^+$) calcd for $C_{39}H_{42}FN_5O_2$ 631.33, found 632.5.

Example 9: Preparation of (R)—N-((5-fluoro-2-hydroxyphenyl)(1H-indole-2-yl)methyl)-4'-(4-(1-methylpiperidine-4-yl)piperazine-1-yl)-[1,1'-biphenyl]-3-carboxamide

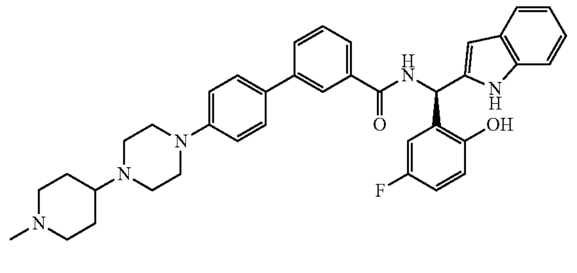 [SMILES: CN1CCC(N2CCN(c3ccc(-c4cccc(C(=O)N[C@@H](c5cc6ccccc6[nH]5)c5cc(F)ccc5O)c4)cc3)CC2)CC1]

(R)—N-((5-fluoro-2-hydroxyphenyl)(1H-indole-2-yl)methyl)-4'-(4-(1-methylpiperidine-4-yl)piperazine-1-yl)-[1,1'-biphenyl]-3-carboxamide [Example 9] (5.4 mg, 22%) was prepared by a method similar to the method described in [Example 1].

$^1$H NMR (300 MHz, methanol-$d_4$) δ 8.13 (t, J=1.8 Hz, 1H), 7.84 (dt, J=7.7, 1.4 Hz, 1H), 7.79 (dt, J=7.9, 1.4 Hz, 1H), 7.66 (d, J=8.7 Hz, 2H), 7.54 (t, J=7.7 Hz, 1H), 7.47 (dt, J=7.7, 1.1 Hz, 1H), 7.35 (d, J=8.1 Hz, 1H), 7.12 (d, J=8.9 Hz, 2H), 7.09-7.03 (m, 2H), 6.98 (ddd, J=8.0, 7.1, 1.1 Hz, 1H), 6.95-6.84 (m, 3H), 6.21 (d, J=1.0 Hz, 1H), 3.73 (d, J=12.9 Hz, 3H), 3.56 (d, J=16.5 Hz, 9H), 3.16 (d, J=13.2 Hz, 2H), 2.93 (s, 3H), 2.50 (d, J=13.7 Hz, 2H), 2.13 (d, J=13.2 Hz, 2H).

<u>Scheme 11.</u>

General Formula 11

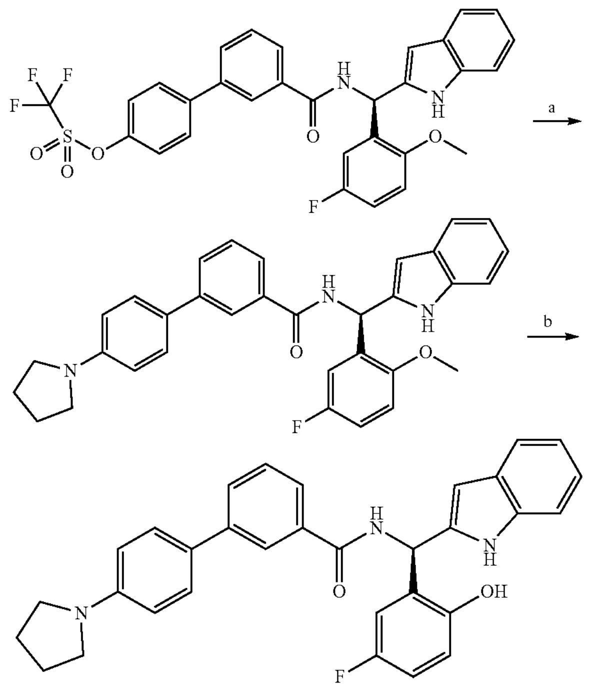

Reagents and conditions: (a) pyrrolidine, $Pd(OAc)_2$, Xantphos, $Cs_2CO_3$, dioxane, 80° C., overnight; (b) 1M $BBr_3$ dissolved in $CH_2Cl_2$, 0° C. to rt, 30 minutes.

Preparative Example 25: Preparation of (R)—N-((5-fluoro-2-methoxyphenyl)(1H-indole-2-yl)methyl)-4'-(pyrrolidine-1-yl)-[1,1'-biphenyl]-3-carboxamide

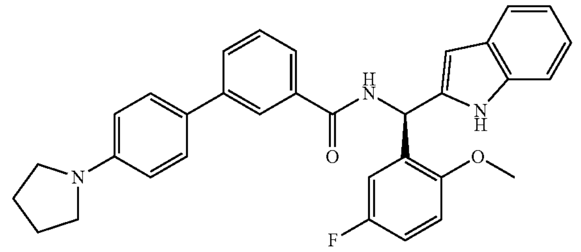 [SMILES: COc1ccc(F)cc1[C@@H](NC(=O)c1cccc(-c2ccc(N3CCCC3)cc2)c1)c1cc2ccccc2[nH]1]

Pyrrolidine (25 mg, 0.35 mmol), (R)-3'-(((5-fluoro-2-methoxyphenyl)(1H-indole-2-yl)methyl)carbamoyl)-[1,1'-biphenyl]-4-yl-trifluoromethanesulfonate [Preparative Example 13] (222 mg, 0.37 mmol), $Pd(OAc)_2$ (8 mg, 0.03 mmol), Xantphos (20 mg, 0.03 mmol), and cesium carbonate (137 mg, 0.42 mmol) were degassed in anhydrous 1,4-dioxane (1.9 mL) for 10 minutes. The stirred suspension was heated at 80° C. overnight, diluted with ethyl acetate, and washed with water and brine. The organic layer was dried over magnesium sulfate and concentrated. The residue was purified by MPLC to give (R)—N-((5-fluoro-2-methoxyphenyl)(1H-indole-2-yl)methyl)-4'-(pyrrolidine-1-yl)-[1,1'-biphenyl]-3-carboxamide [Preparative Example 25] as a yellow solid (yield: 7%): LC-MS ($M+H^+$) calcd for $C_{33}H_{30}FN_3O_2$ 519.62, found 520.9.

Example 10: Preparation of (R)—N-((5-fluoro-2-hydroxyphenyl)(1H-indole-2-yl)methyl)-4'-(pyrrolidine-1-yl)-[1,1'-biphenyl]-3-carboxamide

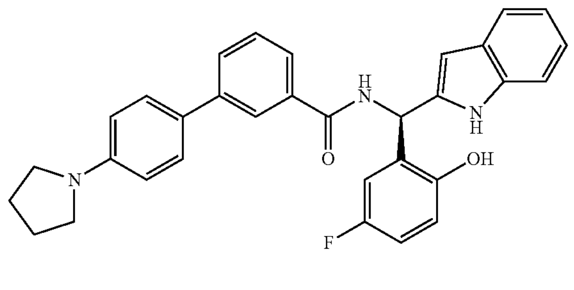 [SMILES: O=C(N[C@@H](c1cc2ccccc2[nH]1)c1cc(F)ccc1O)c1cccc(-c2ccc(N3CCCC3)cc2)c1]

(R)—N-((5-fluoro-2-hydroxyphenyl)(1H-indole-2-yl)methyl)-4'-(pyrrolidine-1-yl)-[1,1'-biphenyl]-3-carboxamide [Example 10] (28%) was prepared by a method similar to the method described in [Example 1].

$^1$H NMR (500 MHz, methanol-$d_4$) δ 9.23 (d, J=8.3 Hz, 1H), 8.13 (s, 1H), 7.78 (t, J=7.0 Hz, 2H), 7.64 (d, J=8.6 Hz, 2H), 7.51 (t, J=7.8 Hz, 1H), 7.46 (dt, J=7.9, 1.0 Hz, 1H), 7.35 (dt, J=8.2, 1.0 Hz, 1H), 7.10-7.04 (m, 2H), 6.98 (ddd, J=7.9, 7.0, 1.0 Hz, 1H), 6.95-6.91 (m, 1H), 6.90-6.85 (m, 4H), 6.20 (t, J=1.0 Hz, 1H), 3.44 (s, 4H), 2.14-2.08 (m, 4H); LC-MS (M+H$^+$) calcd for $C_{32}H_{28}FN_3O_2$ 505.22, found 506.6.

Scheme 12.

General Formula 12

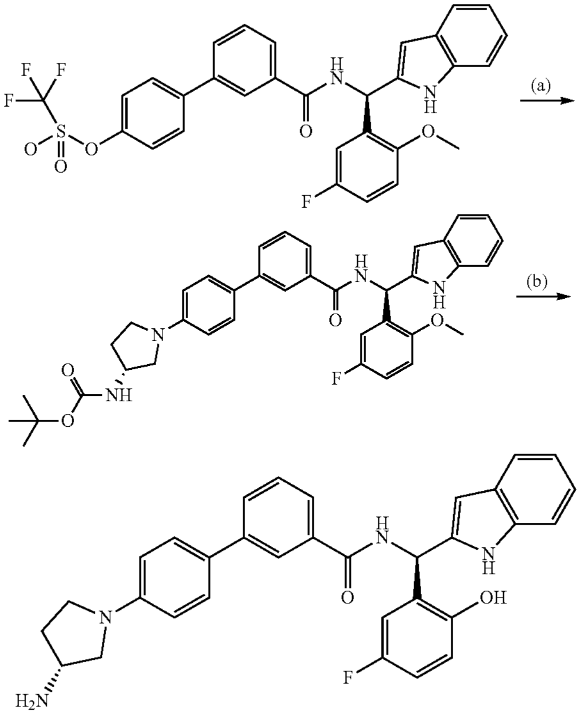

Reagents and conditions:
(a) tert-butyl (R)-pyrrolidine-3-ylcarbamate, $Pd(OAc)_2$, Xantphos. dioxane, 80° C., overnight;
(b) 1 M $BBr_3$ dissolved in $CH_2Cl_2$, 0° C. to rt, 30 mintues.

Preparative Example 26: Preparation of tert-butyl ((R)-1-(3'-(((R)-(5-fluoro-2-methoxyphenyl)(1H-indole-2-yl)methyl)carbamoyl)-[1,1'-biphenyl]-4-yl) pyrrolidine-3-yl)carbamate

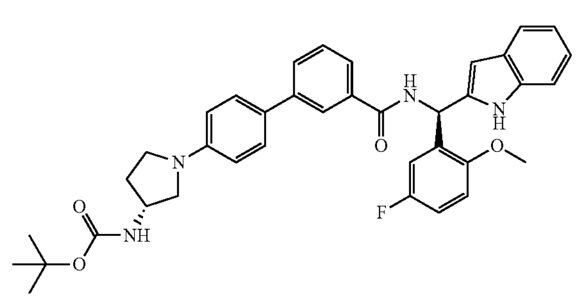 [SMILES: COc1ccc(F)cc1[C@@H](NC(=O)c1cccc(-c2ccc(N3CC[C@@H](NC(=O)OC(C)(C)C)C3)cc2)c1)c1cc2ccccc2[nH]1]

Tert-butyl (R)-pyrrolidine-3-ylcarbamate (65 mg, 0.35 mmol), (R)-3'-(((5-fluoro-2-methoxyphenyl)(1H-indole-2-yl)methyl)carbamoyl)-[1,1'-biphenyl]-4-yl-trifluoromethanesulfonate [Preparative Example 13] (222 mg, 0.37 mmol), $Pd(OAc)_2$ (8 mg, 0.03 mmol), Xantphos (20 mg, 0.03 mmol), and cesium carbonate (137 mg, 0.42 mmol) were degassed in anhydrous 1,4-dioxane (1.9 mL) for 10 minutes. The stirred suspension was heated at 80° C. overnight, diluted with ethyl acetate, and washed with water and brine. The organic layer was dried over magnesium sulfate and concentrated. The residue was purified by MPLC to give tert-butyl ((R)-1-(3'-(((R)-(5-fluoro-2-methoxyphenyl)(1H-indole-2-yl)methyl)carbamoyl)-[1,1'-biphenyl]-4-yl)pyrrolidine-3-yl)carbamate [Preparative Example 26] (14 mg, 7%) as a yellow solid: LC-MS (M+H$^+$) calcd for $C_{38}H_{39}FN_4O_4$ 634.29, found 635.7.

Example 11: Preparation of 4'-((R)-3-aminopyrrolidine-1-yl)-N—((R)-(5-fluoro-2-hydroxyphenyl)(1H-indole-2-yl)methyl)-[1,1'-biphenyl]-3-carboxamide

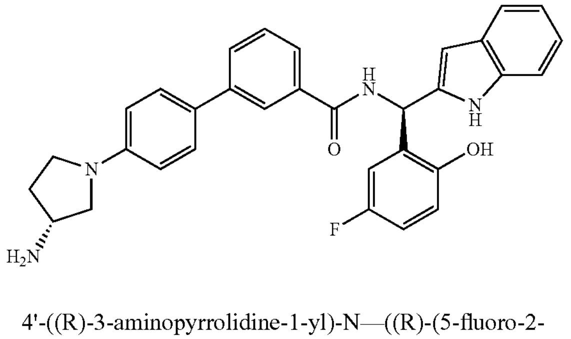

4'-((R)-3-aminopyrrolidine-1-yl)-N—((R)-(5-fluoro-2-hydroxyphenyl)(1H-indole-2-yl)methyl)-[1,1'-biphenyl]-3-carboxamide [Example 11] (18%) was prepared by a method similar to the method described in [Example 1].

$^1$H NMR (500 MHz, methanol-$d_4$) δ 9.22 (d, J=8.3 Hz, 1H), 8.11 (t, J=1.8 Hz, 1H), 7.81-7.73 (m, 2H), 7.70-7.63 (m, 1H), 7.62-7.55 (m, 3H), 7.51 (t, J=7.8 Hz, 1H), 7.48-7.46 (m, 1H), 7.37-7.33 (m, 1H), 7.10-7.05 (m, 2H), 6.98 (ddd, J=8.0, 7.0, 1.0 Hz, 1H), 6.95-6.85 (m, 3H), 6.79-6.74 (m, 2H), 6.21 (t, J=1.0 Hz, 1H), 4.06 (tt, J=6.5, 3.6 Hz, 1H), 3.69-3.61 (m, 2H), 3.49 (dd, J=10.7, 3.3 Hz, 1H), 3.42 (td, J=9.2, 4.9 Hz, 1H), 2.50 (ddt, J=13.5, 8.9, 6.8 Hz, 1H), 2.19 (ddt, J=12.9, 8.3, 4.5 Hz, 1H); LC-MS (M+H$^+$) calcd for $C_{32}H_{29}FN_4O_2$ 520.23, found 520.6.

Scheme 13.

General Formula 13

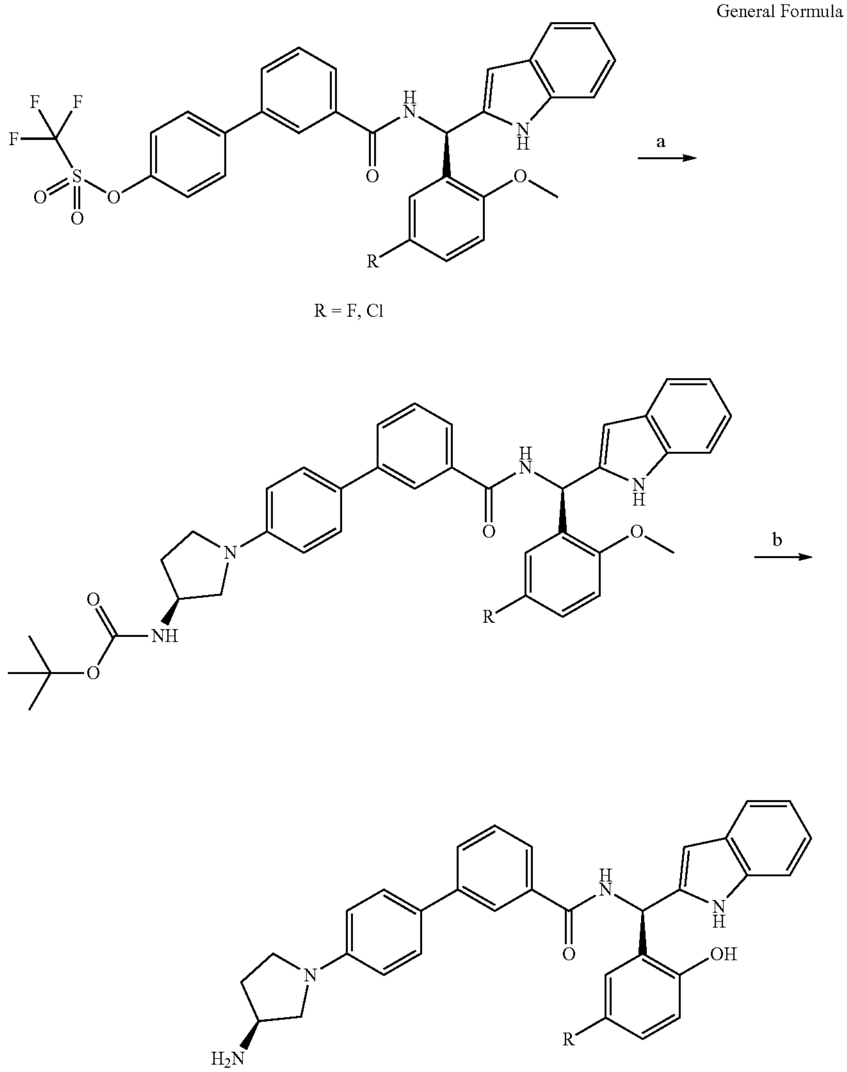

Reagents and conditions: (a) tert-butyl (S)-pyrrolidine-3-ylcarbamate, $Pd(OAc)_2$, Xantphos, $Cs_2CO_3$, dioxane, 80° C., overnight; (b) 1M $BBr_3$ dissolved in $CH_2Cl_2$, 0° C. to rt, 30 minutes.

Preparative Example 27: Preparation of tert-butyl ((S)-1-(3'-(((R)-(5-fluoro-2-methoxyphenyl)(1H-indole-2-yl)methyl)carbamoyl)-[1,1'-biphenyl]-4-yl)pyrrolidine-3-yl)carbamate

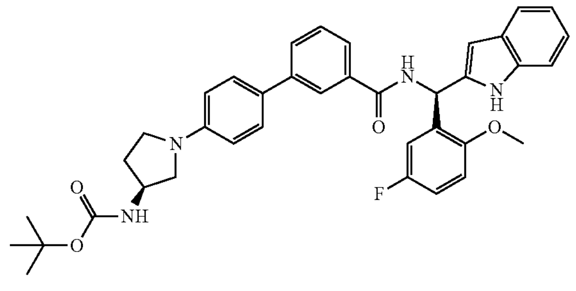 [SMILES: COc1ccc(F)cc1[C@@H](NC(=O)c1cccc(-c2ccc(N3CC[C@H](NC(=O)OC(C)(C)C)C3)cc2)c1)c1cc2ccccc2[nH]1]

Tert-butyl (S)-pyrrolidine-3-ylcarbamate (65 mg, 0.35 mmol), (R)-3'-(((5-fluoro-2-methoxyphenyl)(1H-indole-2-yl)methyl)carbamoyl)-[1,1'-biphenyl]-4-yl-trifluoromethanesulfonate [Preparative Example 13] (222 mg, 0.37 mmol), $Pd(OAc)_2$ (8 mg, 0.03 mmol), Xantphos (20 mg, 0.03 mmol), and cesium carbonate (137 mg, 0.42 mmol) were degassed in anhydrous 1,4-dioxane (1.9 mL) for 10 minutes. The stirred suspension was heated at 80° C. overnight, diluted with ethyl acetate, and washed with water and brine. The organic layer was dried over magnesium sulfate and concentrated. The residue was purified by MPLC to give tert-butyl ((S)-1-(3'-(((R)-(5-fluoro-2-methoxyphenyl)(1H-indole-2-yl)methyl)carbamoyl)-[1,1'-biphenyl]-4-yl)pyrrolidine-3-yl)carbamate [Preparative Example 27] (65 mg, 28%) as a brown solid: LC-MS $(M+H^+)$ calcd for $C_{38}H_{39}FN_4O_4$ 634.29, found 635.5.

Preparative Example 28: Preparation of tert-butyl ((S)-1-(3'-(((R)-(5-chloro-2-methoxyphenyl)(1H-indole-2-yl)methyl)carbamoyl)-[1,1'-biphenyl]-4-yl) pyrrolidine-3-yl)carbamate

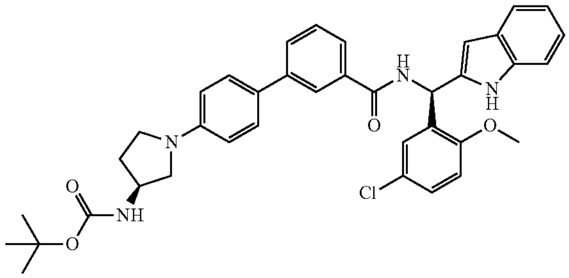 [SMILES: COc1ccc(Cl)cc1[C@@H](NC(=O)c1cccc(-c2ccc(N3CC[C@H](NC(=O)OC(C)(C)C)C3)cc2)c1)c1cc2ccccc2[nH]1]

Tert-butyl ((S)-1-(3'-(((R)-(5-chloro-2-methoxyphenyl) (1H-indole-2-yl)methyl)carbamoyl)-[1,1'-biphenyl]-4-yl) pyrrolidine-3-yl)carbamate [Preparative Example 28] (40%) was prepared by a method similar to the method described in [Preparative Example 27]: LC-MS (M+H$^+$) calcd for $C_{38}H_{39}ClN_4O_4$ 650.27, found 651.9.

Example 12: Preparation of 4'-((S)-3-aminopyrrolidine-1-yl)-N—((R)-(5-fluoro-2-hydroxyphenyl)(1H-indole-2-yl)methyl)-[1,1'-biphenyl]-3-carboxamide

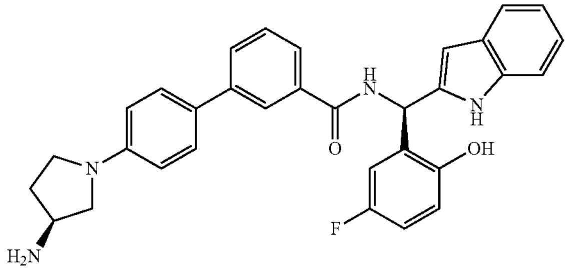 [SMILES: N[C@H]1CCN(c2ccc(-c3cccc(C(=O)N[C@@H](c4cc5ccccc5[nH]4)c4cc(F)ccc4O)c3)cc2)C1]

4'-((S)-3-aminopyrrolidine-1-yl)-N—((R)-(5-fluoro-2-hydroxyphenyl)(1H-indole-2-yl)methyl)-[1,1'-biphenyl]-3-carboxamide [Example 12] (21%) was prepared by a method similar to the method described in [Example 1].

$^1$H NMR (500 MHz, methanol-$d_4$) δ 9.22 (d, J=8.3 Hz, 1H), 8.11 (d, J=1.9 Hz, 1H), 7.78 (t, J=8.1 Hz, 2H), 7.67 (t, J=6.4 Hz, 1H), 7.64-7.57 (m, 3H), 7.51 (t, J=7.7 Hz, 1H), 7.46 (d, J=7.9 Hz, 1H), 7.35 (d, J=8.1 Hz, 1H), 7.07 (t, J=7.4 Hz, 2H), 6.98 (t, J=7.5 Hz, 1H), 6.92 (dd, J=8.5, 2.8 Hz, 1H), 6.88 (dt, J=8.3, 5.2 Hz, 2H), 6.79-6.75 (m, 2H), 6.20 (s, 1H), 4.06 (s, 1H), 3.65 (dd, J=10.0, 6.5 Hz, 2H), 3.53-3.47 (m, 1H), 3.43 (td, J=9.1, 4.9 Hz, 1H), 2.51 (dq, J=14.7, 7.3 Hz, 1H), 2.20 (td, J=8.3, 4.0 Hz, 1H).

Example 13: Preparation of 4'-((S)-3-aminopyrrolidine-1-yl)-N—((R)-(5-chloro-2-hydroxyphenyl)(1H-indole-2-yl)methyl)-[1,1'-biphenyl]-3-carboxamide

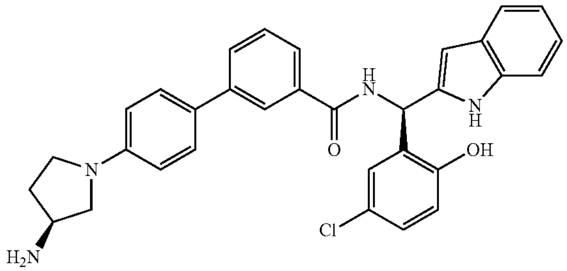 [SMILES: N[C@H]1CCN(c2ccc(-c3cccc(C(=O)N[C@@H](c4cc5ccccc5[nH]4)c4cc(Cl)ccc4O)c3)cc2)C1]

4'-((S)-3-aminopyrrolidine-1-yl)-N—((R)-(5-chloro-2-hydroxyphenyl)(1H-indole-2-yl)methyl)-[1,1'-biphenyl]-3-carboxamide [Example 13] (5.2%) was prepared by a method similar to the method described in [Example 1].

$^1$H NMR (300 MHz, methanol-$d_4$) δ 9.20 (d, J=8.2 Hz, 1H), 8.11 (s, 1H), 7.78 (t, J=6.2 Hz, 2H), 7.62 (d, J=8.6 Hz, 2H), 7.50 (dd, J=16.3, 8.0 Hz, 2H), 7.37-7.29 (m, 2H), 7.17 (dd, J=8.6, 2.6 Hz, 1H), 7.08 (t, J=7.5 Hz, 1H), 6.98 (t, J=7.4 Hz, 1H), 6.88 (d, J=8.5 Hz, 2H), 6.77 (d, J=8.6 Hz, 2H), 6.20 (s, 1H), 4.07 (s, 1H), 3.66 (dd, J=10.7, 5.7 Hz, 2H), 3.53-3.39 (m, 2H), 2.52 (dq, J=14.9, 7.0 Hz, 1H), 2.27-2.12 (m, 1H).

The structures of the compounds prepared in Examples 1-13 are summarized and shown in Table 1 below.

TABLE 1

| Example | Structure |
| --- | --- |
| 1 | 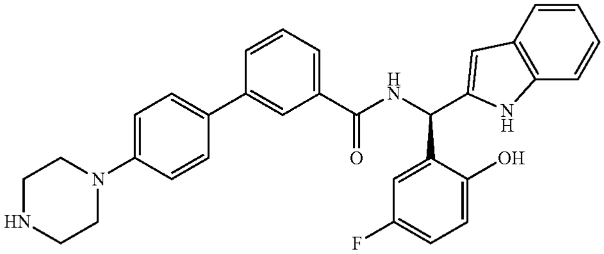 [SMILES: O=C(N[C@@H](c1cc2ccccc2[nH]1)c1cc(F)ccc1O)c1cccc(-c2ccc(N3CCNCC3)cc2)c1] |

TABLE 1-continued
| Example | Structure |
| --- | --- |
| 2 | 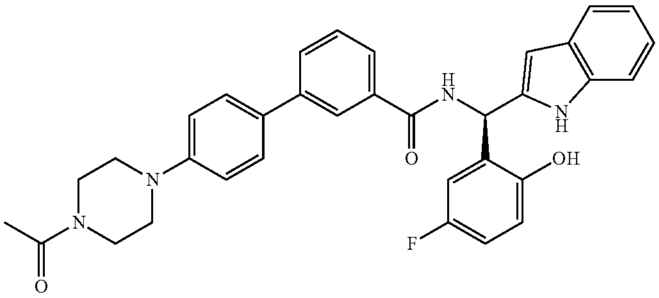 [SMILES: CC(=O)N1CCN(c2ccc(-c3cccc(C(=O)N[C@@H](c4cc5ccccc5[nH]4)c4cc(F)ccc4O)c3)cc2)CC1] |
| 3 | 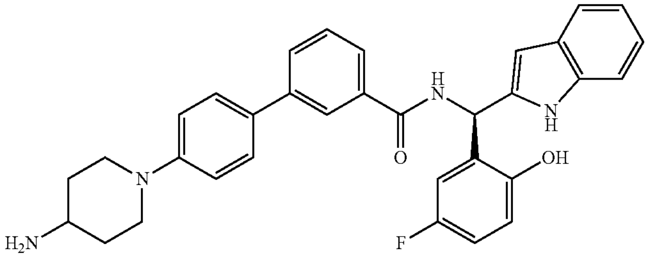 [SMILES: NC1CCN(c2ccc(-c3cccc(C(=O)N[C@@H](c4cc5ccccc5[nH]4)c4cc(F)ccc4O)c3)cc2)CC1] |
| 4 | 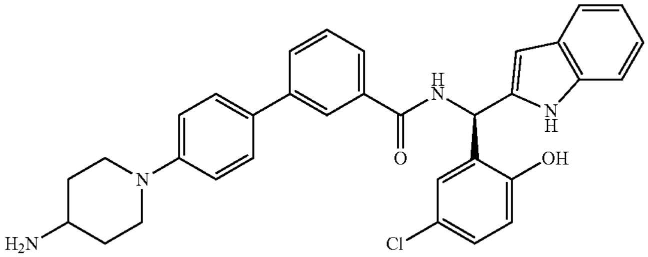 [SMILES: NC1CCN(c2ccc(-c3cccc(C(=O)N[C@@H](c4cc5ccccc5[nH]4)c4cc(Cl)ccc4O)c3)cc2)CC1] |
| 5 | 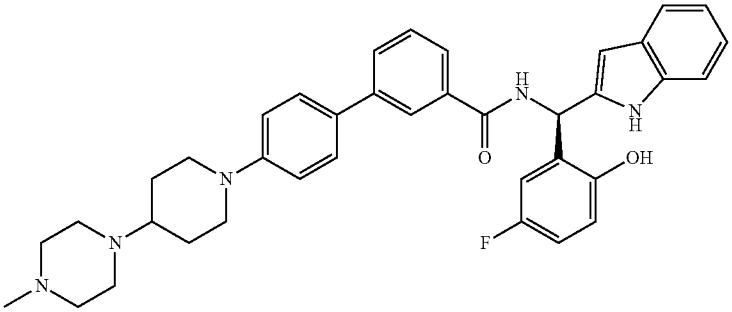 [SMILES: CN1CCN(C2CCN(c3ccc(-c4cccc(C(=O)N[C@@H](c5cc6ccccc6[nH]5)c5cc(F)ccc5O)c4)cc3)CC2)CC1] |
| 6 | 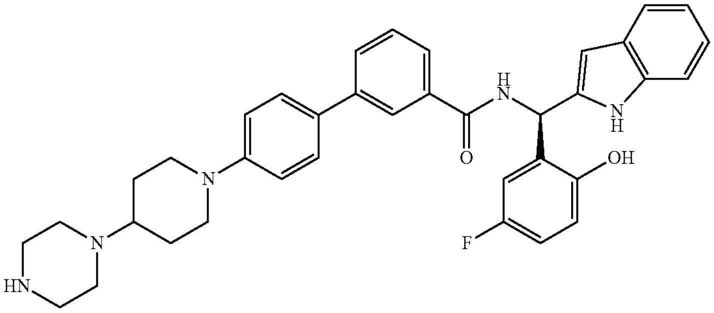 [SMILES: O=C(N[C@@H](c1cc2ccccc2[nH]1)c1cc(F)ccc1O)c1cccc(-c2ccc(N3CCC(N4CCNCC4)CC3)cc2)c1] |

TABLE 1-continued
| Example | Structure |
| --- | --- |
| 7 | 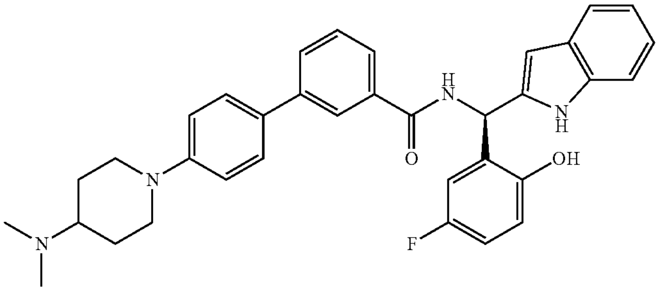 [SMILES: CN(C)C1CCN(c2ccc(-c3cccc(C(=O)N[C@@H](c4cc5ccccc5[nH]4)c4cc(F)ccc4O)c3)cc2)CC1] |
| 8 | 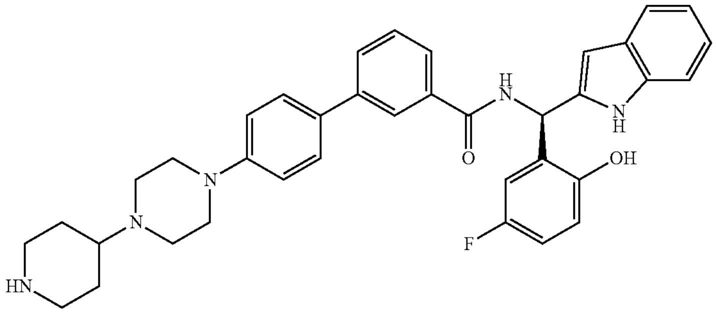 |
| 9 | 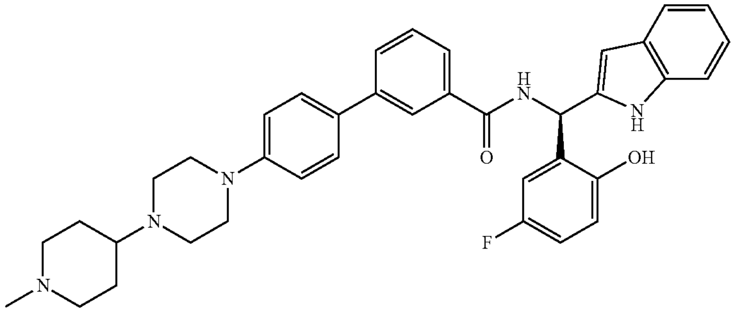 [SMILES: CN1CCC(N2CCN(c3ccc(-c4cccc(C(=O)N[C@@H](c5cc6ccccc6[nH]5)c5cc(F)ccc5O)c4)cc3)CC2)CC1] |
| 10 | 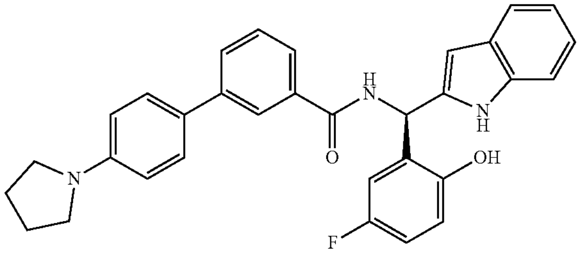 [SMILES: O=C(N[C@@H](c1cc2ccccc2[nH]1)c1cc(F)ccc1O)c1cccc(-c2ccc(N3CCCC3)cc2)c1] |
| 11 | 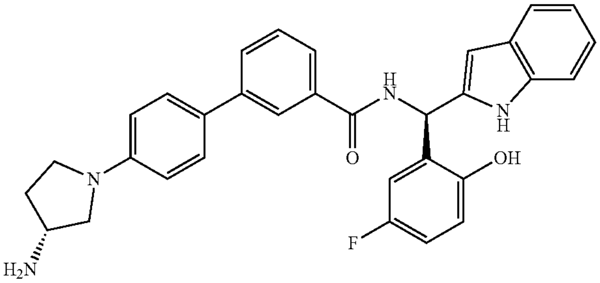 [SMILES: N[C@@H]1CCN(c2ccc(-c3cccc(C(=O)N[C@@H](c4cc5ccccc5[nH]4)c4cc(F)ccc4O)c3)cc2)C1] |

TABLE 1-continued

| Example | Structure |
|---|---|
| 12 | 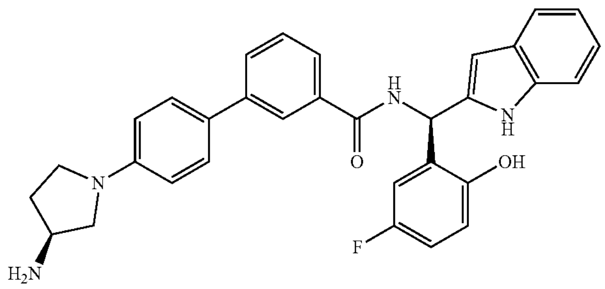 [SMILES: N[C@H]1CCN(c2ccc(-c3cccc(C(=O)N[C@@H](c4cc5ccccc5[nH]4)c4cc(F)ccc4O)c3)cc2)C1] |
| 13 | 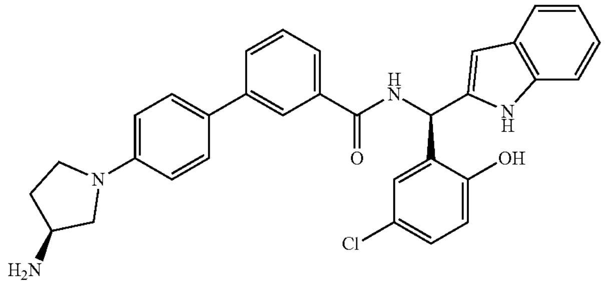 [SMILES: N[C@H]1CCN(c2ccc(-c3cccc(C(=O)N[C@@H](c4cc5ccccc5[nH]4)c4cc(Cl)ccc4O)c3)cc2)C1] |

Experimental Example 1: Measurement of Inhibitory Capacity Against EGFR L858R/T790M/C797S In order to confirm the inhibitory capacity of the compounds prepared in Examples 1 to 13 provided in one aspect of the present invention against EGFR mutation, the following experiment was performed.

Particularly, the activity of the compounds of the present invention against EGFR mutant enzyme was measured using the HTRF system of Cisbio Co. As an EGFR L858R/T790M/C797S mutant enzyme, a protein provided by SignalChem was purchased and used as an enzyme source.

The composition of the assay buffer used for the activity measurement was as follows: 50 mM Tris-HCl (pH 7.5), 100 mM NaCl, 7.5 mM $MgCl_2$, 3 mM KCl, 0.01% Tween 20, 0.1% BSA, and 1 mM DTT. Herein, an enzyme reaction was performed using a peptide substrate labeled with ATP at the concentration of 1 mM and biotin at the concentration of 0.5 μM. The analysis of the EGFR activity inhibitory effect of the compounds was performed according to the following analytical reaction recipe.

Component 1: 4 μl of EGFR mutant enzyme

Component 2: 2 μl of compound solution

Component 3: 4 μl of ATP and biotin-labeled peptide mixture

The enzyme reaction was initiated by mixing the component 1 and the component 2 first and then adding the component 3 thereto. After reacting the mixture at 37° C. for 2 hours, 10 μl of a measurement solution consisting of streptavidin-XL665 and europium-labeled anti-phosphotyrosine antibody provided by Cisbio was added to the enzyme reaction solution, followed by reaction at room temperature for 1 hour. Finally, the ratio of the fluorescence values at 615 nm and 665 nm was calculated using Envision equipment of Perkin-Elmer to quantitatively measure the enzyme activity and confirm the inhibitory ability of the compounds. The values measured at 7 concentrations of the compound were analyzed using Prism program (version 5.01, Graphpad Software, Inc.), and the $IC_{50}$ value, an index of the inhibitory ability of the compound, was calculated.

The results are shown in Table 2.

TABLE 2

| Example | EGFR L858R/T790M/C797S $IC_{50}$ (μM) |
|---|---|
| 1 | 0.046 |
| 2 | 0.061 |
| 3 | 0.007 |
| 4 | 0.64 |
| 5 | 2.6 |
| 6 | 0.19 |
| 7 | 0.16 |
| 8 | 0.14 |
| 9 | 0.072 |
| 10 | 5.9 |
| 11 | 0.16 |
| 12 | 0.18 |
| 13 | >10 |

As shown in Table 2, among the compounds of Examples 1 to 13 provided in one aspect of the present invention, the compounds of Examples 1 and 3 exhibited excellent inhibitory capacity against EGFR L858R/T790M/C797S mutation.

Experimental Example 2: Evaluation of Anticancer Activity in BaF3 Cells Overexpressed with Various EGFR Mutations In order to confirm that the compound represented by formula 1 according to the present invention acted as an allosteric inhibitor against EGFR wild-type and mutants, the inhibitory effect on EGFR wild-type and mutants in Ba/F3 cell line was evaluated. In addition, in order to evaluate the cellular activity when the compound according to the present invention was co-administered with an existing drug, the cellular activity according to the combined administration was evaluated using Cetuximab used alone or in combination with chemotherapy in metastatic colorectal cancer and metastatic squamous head and neck cancer.

Particularly, the activity of the compound of the present invention against the wild-type and mutant Ba/F3 EGFR cell lines was measured as follows using the CellTiter-Glo system of Promega. CellTiter-Glo assay is a method to confirm the cell viability by measuring ATP present in cells in culture state. Ba/F3 EGFR wild-type (WT) and Ba/F3 EGFR del19 (D), Ba/F3 EGFR del19/T790M (DT), Ba/F3 del19/T790M/C797S (DTC), Ba/F3 EGFR L858R (L), Ba/F3 EGFR L858R/T790M (LT), and Ba/F3 L858R/T790M/C797S (LTC) mutant cell lines were purchased from Crown Bioscience and used. Ba/F3 EGFR wild-type (WT) and Ba/F3 EGFR del19 (D), Ba/F3 EGFR del19/T790M (DT), Ba/F3 del19/T790M/C797S (DTC), Ba/F3 EGFR L858R (L), Ba/F3 EGFR L858R/T790M (LT), and Ba/F3 L858R/T790M/C797S (LTC) mutant cell lines were cultured in RPMI containing 10% FBS and 1% penicillin-streptomycin in a 37° C., 5% $CO_2$ incubator.

Analysis of the cell survival inhibitory effect of the compound according to each EGFR mutant was performed according to the following analytical reaction recipe.

BaF3 cells were aliquoted in a 96 well cell culture plate at the density of 2500 cells/50 ul per well, to which 50 ul of the compound represented by formula 1 was treated at the concentrations of 0, 0.03, 0.1, 0.3, and 1 μM. The plate treated with the compound was reacted in a 37° C. incubator for 72 hours, and then left at room temperature for 30 minutes according to the CellTiter-Glo assay instruction to maintain the plate temperature at room temperature. Thereafter, 100 μl of CellTiter-Glo reagent was treated to each well of the plate, followed by shaking incubation at room temperature for 10 minutes. Finally, the ratio of the fluorescence values at 570 nm was quantitatively measured using a luminometer, and the ability of the compound to inhibit cell viability was confirmed. The values measured at 5 concentrations (0, 0.03, 0.1, 0.3, and 1 μM) of the compound were analyzed using Prism program (version 5.01, Graphpad Software, Inc.), and the $IC_{50}$ value, an index of the inhibitory ability of the compound, was calculated.

Figure 2:
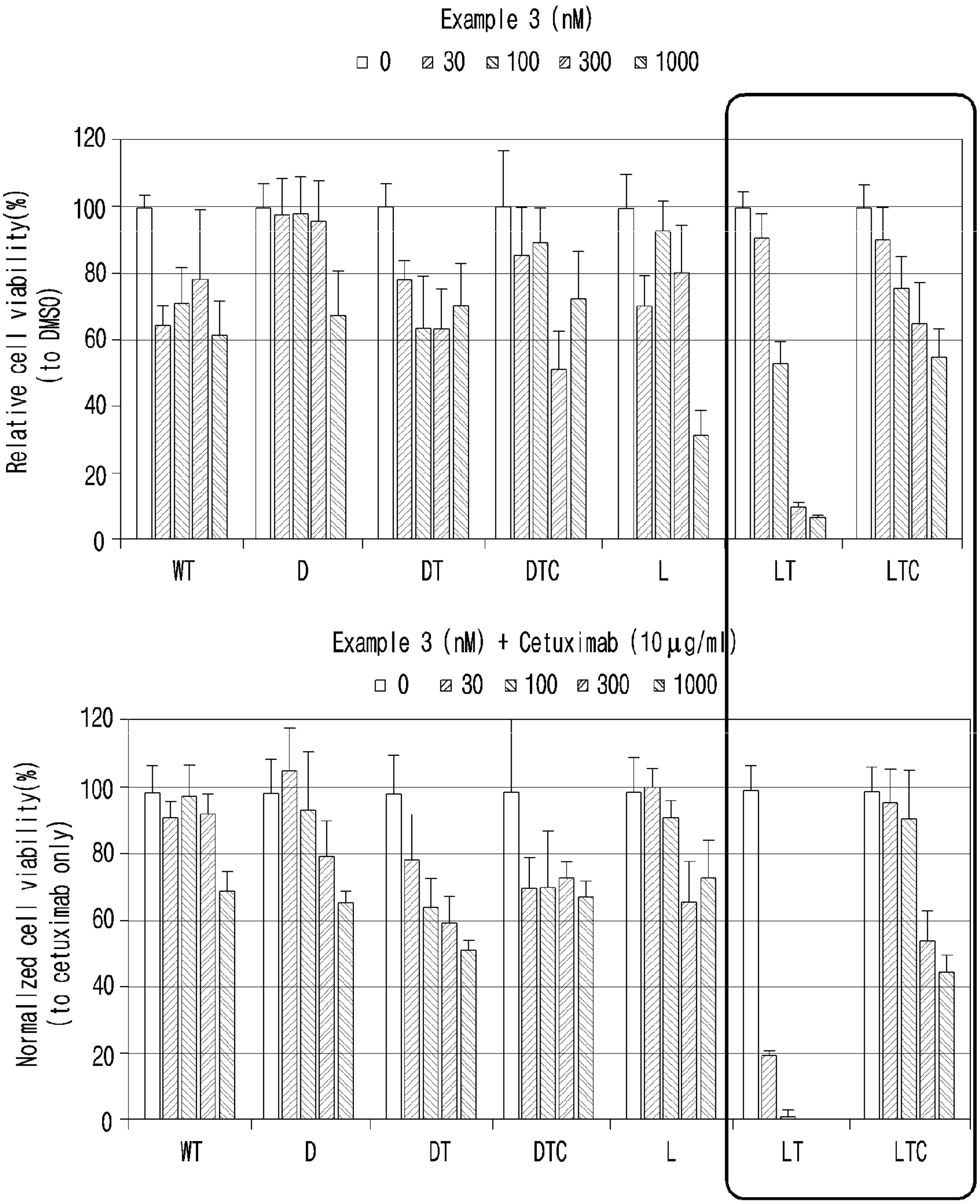

The results are shown in FIG. 1 and FIG. 2.

FIG. 1 and FIG. 2 are a graph showing the results of evaluating the anticancer activity when BaF3 cells overexpressing various EGFR mutations were treated with the example compound provided in one aspect of the present invention alone or in combination with cetuximab, known as an EGFR antagonist.

As shown in FIG. 1 and FIG. 2, when the compounds of Examples 1 and 3 provided in one aspect of the present invention were treated in combination with cetuximab, the synergistic anticancer activity was shown in cells overexpressed with EGFR L858R/T790M and EGFR L858R/T790M/C797S.

For reference, "to cetuximab only" on the Y-axis of FIG. 1 and FIG. 2 means that the cell viability (%) when cetuximab is treated alone is considered as 100%.

Manufacturing Example 1: Preparation of Powders

| Derivative represented by formula 1 | 2 g |
|---|---|
| Lactose | 1 g |

Powders were prepared by mixing all the above components, which were filled in airtight packs according to the conventional method for preparing powders.

Manufacturing Example 2: Preparation of Tablets

| Derivative represented by formula 1 | 100 mg |
|---|---|
| Corn starch | 100 mg |
| Lactose | 100 mg |
| Magnesium stearate | 2 mg |

Tablets were prepared by mixing all the above components by the conventional method for preparing tablets.

Manufacturing Example 3: Preparation of Capsules

| Derivative represented by formula 1 | 100 mg |
|---|---|
| Corn starch | 100 mg |
| Lactose | 100 mg |
| Magnesium stearate | 2 mg |

Capsules were prepared by mixing all the above components, which were filled in gelatin capsules according to the conventional method for preparing capsules.

Manufacturing Example 4: Preparation of Injectable Solutions

| Derivative represented by formula 1 | 100 mg |
|---|---|
| Mannitol | 180 mg |
| $Na_2HPO_4 \cdot 2H_2O$ | 26 mg |
| Distilled water | 2974 mg |

Injectable solutions were prepared by containing all the above components in the amounts indicated according to the conventional method for preparing injectable solutions.

Manufacturing Example 5: Preparation of Health Functional Foods

| Derivative represented by formula 1 | 500 ng |
|---|---|
| Vitamin complex | proper amount |
| Vitamin A acetate | 70 mg |
| Vitamin E | 1.0 mg |
| Vitamin | 0.13 mg |
| Vitamin B2 | 0.15 mg |
| Vitamin B6 | 0.5 mg |
| Vitamin B12 | 0.2 mg |
| Vitamin C | 10 mg |
| Biotin | 10 mg |
| Nicotinamide | 1.7 mg |
| Folic acid | 50 mg |
| Calcium pantothenate | 0.5 mg |
| Minerals | proper amount |
| Ferrous sulfate | 1.75 mg |
| Zinc oxide | 0.82 mg |
| Magnesium carbonate | 25.3 mg |
| Potassium phosphate | 15 mg |
| Calcium phosphate, dibasic | 55 mg |
| Potassium citrate | 90 mg |

-continued

| Derivative represented by formula 1 | 500 ng |
|---|---|
| Calcium carbonate | 100 mg |
| Magnesium chloride | 24.8 mg |

The vitamins and minerals appropriate for health functional foods were mixed according to the preferred mixing ratio but the composition ratio can be adjusted arbitrarily. After mixing the above components according to the conventional method for preparing health functional foods, granules were prepared and the granules were used for the preparation of health functional foods according to the conventional method.

Manufacturing Example 6: Preparation of Health Beverages

| Derivative represented by formula 1 | 500 ng |
|---|---|
| Citric acid | 1000 mg |
| Oligosaccharide | 100 g |
| Maesil (Prunus mume) Extract | 2 g |
| Taurine | 1 g |
| Purified water | up to 900㎖ |

The above constituents were mixed according to the conventional method for preparing health beverages. The mixture was heated at 85° C. for 1 hour with stirring and then filtered. The filtrate was loaded in sterilized containers, which were sealed and sterilized again, stored in a refrigerator until they would be used for the preparation of a composition for health beverages.

The constituents appropriate for favorite beverages were mixed according to the preferred mixing ratio but the composition ratio can be adjusted according to regional and ethnic preferences such as demand class, demand country, and purpose of use, etc.

INDUSTRIAL APPLICABILITY

The benzamide derivative provided in an aspect of the present invention can be used for preventing or treating cancer by suppressing EGFR mutation, and exhibits a remarkable synergy effect on anticancer activity when administered in combination with an EGFR antagonist such as Cetuximab, so that it can be effectively used as an anticancer agent.

What is claimed is:

1. A compound, or an optical isomer thereof, a solvate thereof, a hydrate thereof, or a pharmaceutically acceptable salt thereof, having a structure according to:

[Formula 1]

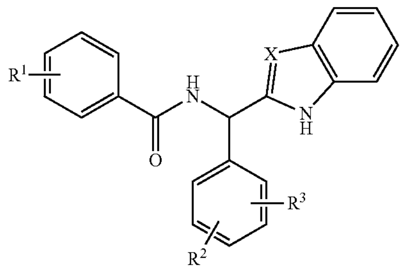

wherein:

$R^1$ is substituted $C_{6-12}$ aryl, wherein, the substituted $C_{6-12}$ aryl is $C_{6-12}$ aryl substituted with unsubstituted or substituted 5~10 membered heterocycloalkyl containing one or more heteroatoms selected from N, O and S, the substituted 5~10 membered heterocycloalkyl is $C_{1-15}$ straight or branched alkylcarbonyl, —$NR^4R^5$, or 5~10 membered heterocycloalkyl substituted with 5~7 membered heterocycloalkyl unsubstituted or substituted with one or more $C_{1-5}$ straight or branched alkyl containing one or more heteroatoms selected from N, O and S, and $R^4$ and $R^5$ are independently hydrogen or $C_{1-15}$ straight or branched alkyl;

$R^2$ is halogen;

$R^3$ is —OH, or $C_{1-15}$ straight or branched alkoxy; and

X is ═CH—, or ═N—.

2. The compound, the optical isomer thereof, the solvate thereof, the hydrate thereof, or the pharmaceutically acceptable salt thereof according to claim 1, wherein:

$R^1$ is substituted $C_{6-12}$ aryl, wherein, the substituted $C_{6-12}$ aryl is $C_{6-12}$ aryl substituted with unsubstituted or substituted 5~10 membered heterocycloalkyl containing one or more heteroatoms selected from N, O and S, the substituted 5~10 membered heterocycloalkyl is $C_{1-10}$ straight or branched alkylcarbonyl, —$NR^4R^5$, or 5~10 membered heterocycloalkyl substituted with 6 membered heterocycloalkyl unsubstituted or substituted with one or more $C_{1-3}$ straight or branched alkyl containing one or more heteroatoms selected from N, O and S, and $R^4$ and $R^5$ are independently hydrogen or $C_{1-10}$ straight or branched alkyl;

$R^2$ is halogen;

$R^3$ is —OH, or $C_{1-10}$ straight or branched alkoxy; and

X is ═CH—, or ═N—.

3. The compound, the optical isomer thereof, the solvate thereof, the hydrate thereof, or the pharmaceutically acceptable salt thereof according to claim 1, wherein:

$R^1$ is

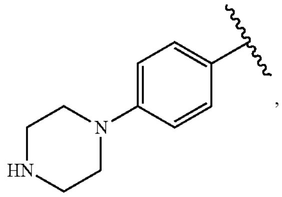

,

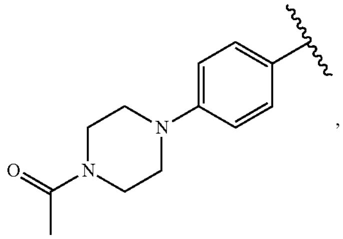

,

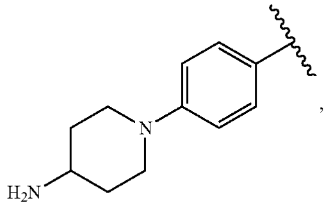

,

-continued

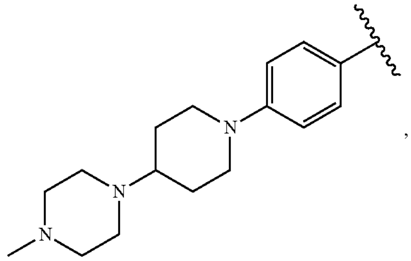

,

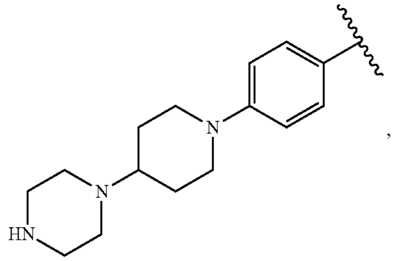

,

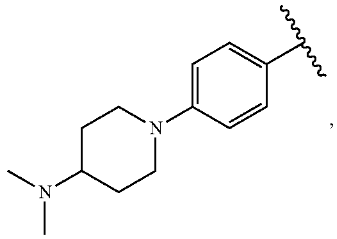

,

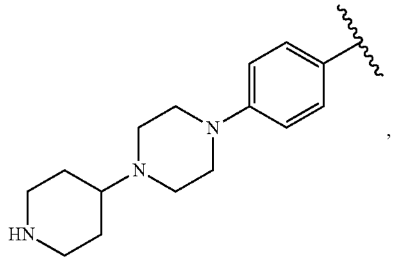

,

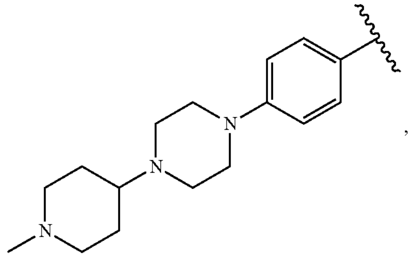

,

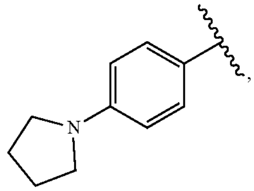

,

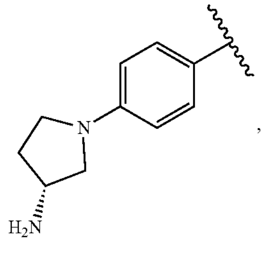

, or

-continued

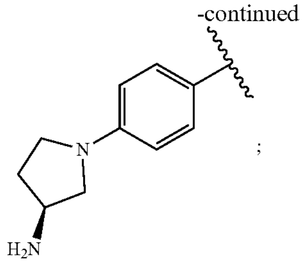

;

$R^2$ is —F, or —Cl;
$R^3$ is —OH; and
X is ═CH—.

4. The compound, the optical isomer thereof, the solvate thereof, the hydrate thereof, or the pharmaceutically acceptable salt thereof according to claim 1, having a structure according to:

[Formula 2]

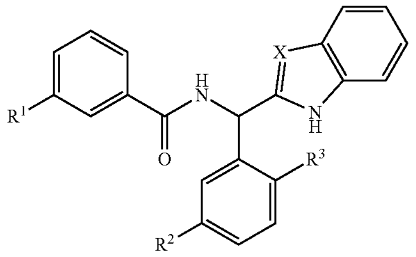

.

5. The compound, the optical isomer thereof, the solvate thereof, the hydrate thereof, or the pharmaceutically acceptable salt thereof according to claim 1, wherein the compound is selected from the following:

(1) (R)—N-((5-fluoro-2-hydroxyphenyl)(1H-indole-2-yl)methyl)-4'-(piperazine-1-yl)-[1,1'-biphenyl]-3-carboxamide;

(2) (R)-4'-(4-acetylpiperazine-1-yl)-N-((5-fluoro-2-hydroxyphenyl)(1H-indole-2-yl)methyl)-[1,1'-biphenyl]-3-carboxamide;

(3) (R)-4'-(4-aminopiperidine-1-yl)-N-((5-fluoro-2-hydroxyphenyl)(1H-indole-2-yl)methyl)-[1,1'-biphenyl]-3-carboxamide;

(4) (R)-4'-(4-aminopiperidine-1-yl)-N-((5-chloro-2-hydroxyphenyl)(1H-indole-2-yl)methyl)-[1,1'-biphenyl]-3-carboxamide;

(5) (R)—N-((5-fluoro-2-hydroxyphenyl)(1H-indole-2-yl)methyl)-4'-(4-(4-methylpiperazine-1-yl)piperidine-1-yl)-[1,1'-biphenyl]-3-carboxamide;

(6) (R)—N-((5-fluoro-2-hydroxyphenyl)(1H-indole-2-yl)methyl)-4'-(4-(piperazine-1-yl)piperidine-1-yl)-[1,1'-biphenyl]-3-carboxamide;

(7) (R)-4'-(4-(dimethylamino)piperidine-1-yl)-N-((5-fluoro-2-hydroxyphenyl)(1H-indole-2-yl)methyl)-[1,1'-biphenyl]-3-carboxamide;

(8) (R)—N-((5-fluoro-2-hydroxyphenyl)(1H-indole-2-yl)methyl)-4'-(4-(piperidine-4-yl)piperazine-1-yl)-[1,1'-biphenyl]-3-carboxamide;

(9) (R)—N-((5-fluoro-2-hydroxyphenyl)(1H-indole-2-yl)methyl)-4'-(4-(1-methylpiperidine-4-yl)piperazine-1-yl)-[1,1'-biphenyl]-3-carboxamide;

(10) (R)—N-((5-fluoro-2-hydroxyphenyl)(1H-indole-2-yl)methyl)-4'-(pyrrolidine-1-yl)-[1,1'-biphenyl]-3-carboxamide;

(11) 4'-((R)-3-aminopyrrolidine-1-yl)-N—((R)-(5-fluoro-2-hydroxyphenyl)(1H-indole-2-yl)methyl)-[1,1'-biphenyl]-3-carboxamide;

(12) 4'-((S)-3-aminopyrrolidine-1-yl)-N—((R)-(5-fluoro-2-hydroxyphenyl)(1H-indole-2-yl)methyl)-[1,1'-biphenyl]-3-carboxamide; and

(13) 4'-((S)-3-aminopyrrolidine-1-yl)-N—((R)-(5-chloro-2-hydroxyphenyl)(1H-indole-2-yl)methyl)-[1,1'-biphenyl]-3-carboxamide.

6. A pharmaceutical composition comprising the compound of claim 1, or an optical isomer thereof, a solvate thereof, a hydrate thereof, or a pharmaceutically acceptable salt thereof, as an active ingredient for use in treating cancer, wherein the cancer is lung cancer, breast cancer, glioma, brain cancer, colorectal cancer, head and neck cancer, stomach cancer, ovarian cancer, cervical cancer, bladder cancer, or endometrial cancer.

7. The pharmaceutical composition according to claim 6, wherein the compound inhibits EGFR (epidermal growth factor receptor) mutation to treat the cancer.

8. The pharmaceutical composition according to claim 7, wherein the EGFR (epidermal growth factor receptor) mutation is at least one selected from EGFR L858R/T790M and EGFR L858R/T790M/C797S.

9. The pharmaceutical composition according to claim 6, wherein the lung cancer is at least one selected from non-small cell lung cancer, small cell lung cancer lung adenocarcinoma, and lung squamous cell carcinoma.

10. A health functional food composition comprising a compound represented by formula 1, an optical isomer thereof, a solvate thereof, a hydrate thereof, or a pharmaceutically acceptable salt thereof as an active ingredient for the prevention or amelioration of cancer.

11. A combination preparation comprising a compound represented by formula 1, an optical isomer thereof, a solvate thereof, a hydrate thereof, or a pharmaceutically acceptable salt thereof; and an EGFR antagonist for treatment of cancer.

12. The combination preparation according to claim 11, wherein the EGFR antagonist is at least one selected from Cetuximab, Erlotinib, Gefitinib, and Panitumumab.

13. A method of treating cancer comprising administering a compound represented by formula 1 of claim 1, an optical isomer thereof, a solvate thereof, a hydrate thereof, or a pharmaceutically acceptable salt thereof to a subject in need, wherein the cancer is lung cancer, breast cancer, glioma, brain cancer, colorectal cancer, head and neck cancer, stomach cancer, ovarian cancer, cervical cancer, bladder cancer, or endometrial cancer.

14. The method according to claim 13, wherein the compound inhibits EGFR (epidermal growth factor receptor) mutation to treat the cancer.

15. The method according to claim 14, wherein the EGFR (epidermal growth factor receptor) mutation is at least one selected from EGFR L858R/T790M and EGFR L858R/T790M/C797S.

16. The method according to claim 13, wherein the lung cancer is at least one selected from non-small cell lung cancer, small cell lung cancer, lung adenocarcinoma, and lung squamous cell carcinoma.

* * * * *